US008956623B2

(12) United States Patent
Kuo et al.

(10) Patent No.: US 8,956,623 B2
(45) **Date of Patent: *Feb. 17, 2015**

(54) RECOMBINANT FUSION INTERFERON FOR ANIMALS

(71) Applicant: SBC Virbac Biotech Co., Ltd., Taipei (TW)

(72) Inventors: Tsun-Yung Kuo, I-Lan (TW); Chung-Chin Wu, I-Lan County (TW); Han-Ting Chen, Taoyuan County (TW)

(73) Assignee: SBC Virbac Limited, Causeway Bay (HK)

( * ) Notice: Subject to any disclaimer, the term of this patent is extended or adjusted under 35 U.S.C. 154(b) by 0 days.

This patent is subject to a terminal disclaimer.

(21) Appl. No.: 13/944,306

(22) Filed: Jul. 17, 2013

(65) Prior Publication Data

US 2014/0030222 A1 Jan. 30, 2014

Related U.S. Application Data

(63) Continuation-in-part of application No. 13/557,139, filed on Jul. 24, 2012.

(51) Int. Cl.

| | |
|---|---|
| ***A61K 39/00*** | (2006.01) |
| ***A61K 38/21*** | (2006.01) |
| ***C07K 1/00*** | (2006.01) |
| ***C07K 14/555*** | (2006.01) |
| ***C07K 16/46*** | (2006.01) |

(52) U.S. Cl.

CPC ............... *C07K 14/555* (2013.01); *C07K 16/46* (2013.01); *C07K 2319/30* (2013.01)

USPC .................... 424/192.1; 424/85.7; 424/185.1; 530/351

(58) Field of Classification Search

None

See application file for complete search history.

(56) References Cited

U.S. PATENT DOCUMENTS

| | | | |
|---|---|---|---|
| 7,244,833 | B2 | 7/2007 | Yu et al. |
| 7,442,371 | B2 | 10/2008 | Yu et al. |
| 7,572,437 | B2 | 8/2009 | Fu et al. |
| 7,833,533 | B2 | 11/2010 | Grubman et al. |
| 8,084,021 | B2 | 12/2011 | Yu et al. |
| 2002/0081664 | A1 | 6/2002 | Lo et al. |
| 2009/0280085 | A1 | 11/2009 | Fu et al. |
| 2012/0128624 | A1 | 5/2012 | Yu et al. |

OTHER PUBLICATIONS

Gong Cheng et al., Characterization of the porcine alpha interferon multigene family, ScienceDirect, Gene, 2006, p. 28-38, vol. 382.

Imre Kacskovics et al., Five Putative Subclasses of Swine IgG identified from the cDNA Sequences of a Single Animal1, The American Association of Immunologists, The Journal of Immunology, p. 3565-3573.

Wei-Hsuan Tang et al., Cloning, Expression, Purification and Antiviral Activity Assessment of Recombinant Porcine IFNalpha-IgG Fusion Protein Expressed by Mammalian Cells, Jul. 25, 2011, Thesis, National Iland University.

*Primary Examiner* — Christine J Saoud

*Assistant Examiner* — Jegatheesan Seharaseyon

(74) *Attorney, Agent, or Firm* — Morris Manning & Martin LLP; Tim Tingkang Xia, Esq.

(57) ABSTRACT

The present invention relates to a recombinant fusion interferon for animals, a pharmaceutical composition thereof, and the use of the recombinant fusion interferon. The recombinant fusion interferon is represented by formula (I) or formula (II), $$\text{(Porcine interferon)-(Linker)}_n\text{-(Porcine immunoglobulin Fc fragment)} \quad \text{(I)}$$

Figure 1:
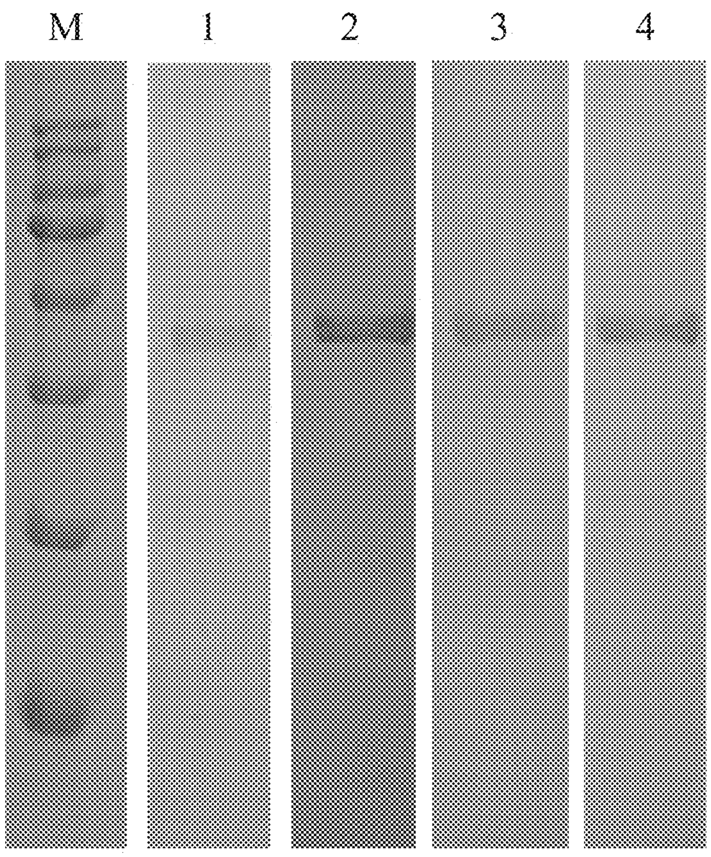
Figure 2A:
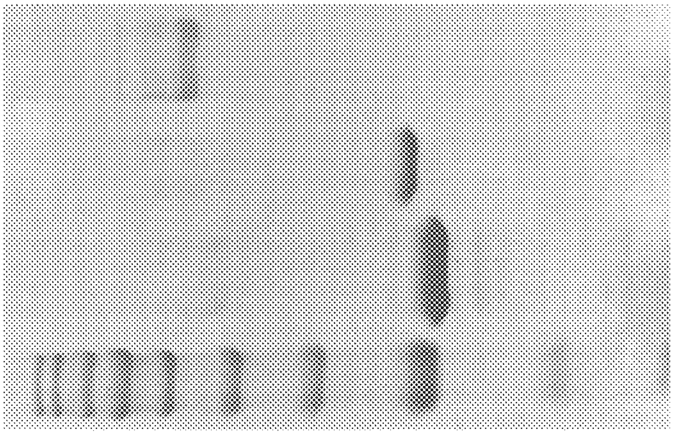
Figure 2B:
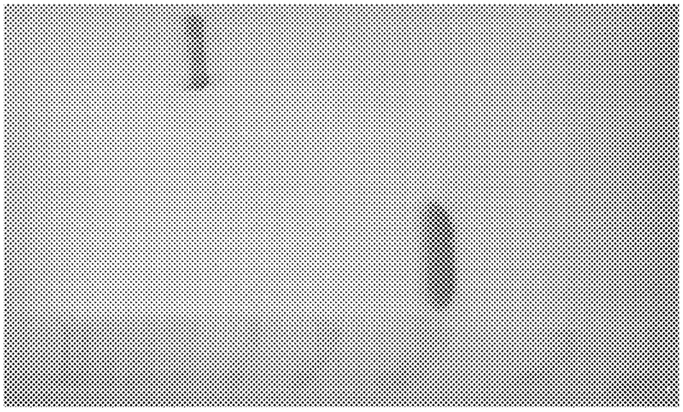
Figure 2C:
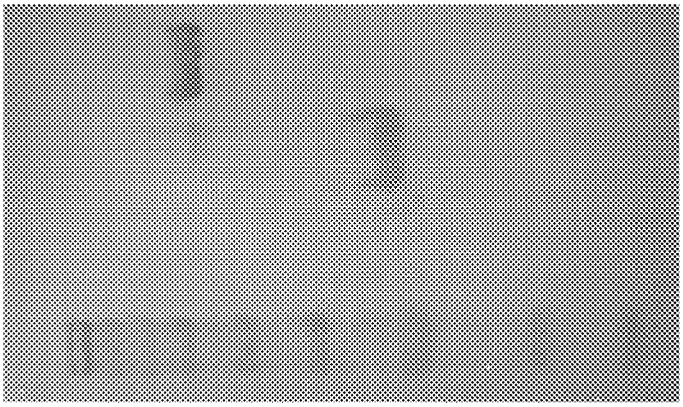

$$\text{(Porcine immunoglobulin Fc fragment)-(Linker)}_n\text{-(Porcine Interferon)} \quad \text{(II)}$$

wherein n is 0 or a positive integer between 1 to 10, the recombinant fusion IFN specifically binds an antibody that specifically binds porcine interferon and an antibody that specifically binds porcine immunoglobulin Fc fragment.

2 Claims, 2 Drawing Sheets

M 1 2 3

M 1 2 3

M 1 2 3

SEQUENCE LISTING

```
<160> NUMBER OF SEQ ID NOS: 51

<210> SEQ ID NO 1
<211> LENGTH: 181
<212> TYPE: PRT
<213> ORGANISM: Sus scrofa

<400> SEQUENCE: 1

Met Ala Pro Thr Ser Ala Phe Leu Thr Ala Leu Val Leu Leu Ser Cys
1               5                   10                  15

Asn Ala Ile Tyr Ser Leu Gly Cys Asp Leu Pro Gln Thr His Ser Leu
            20                  25                  30

Ala His Thr Arg Ala Leu Arg Leu Leu Ala Gln Met Arg Arg Ile Ser
        35                  40                  45

Pro Phe Ser Cys Leu Asp His Arg Arg Asp Phe Gly Phe Pro Gln Glu
    50                  55                  60

Ala Leu Gly Gly Asn Gln Val Gln Lys Ala Gln Ala Met Ala Leu Val
65                  70                  75                  80

His Glu Met Leu Gln Gln Thr Phe Gln Leu Phe Ser Thr Glu Gly Ser
                85                  90                  95

Ala Ala Ala Trp Asp Glu Ser Leu Leu His Gln Phe Cys Thr Gly Leu
            100                 105                 110

Asp Gln Gln Leu Arg Asp Leu Glu Ala Cys Val Met Gln Glu Ala Gly
        115                 120                 125

Leu Glu Gly Thr Pro Leu Leu Glu Glu Asp Ser Ile Leu Ala Val Arg
    130                 135                 140

Lys Tyr Phe His Arg Leu Thr Leu Tyr Leu Gln Glu Lys Ser Tyr Ser
145                 150                 155                 160

Pro Cys Ala Trp Glu Ile Val Arg Ala Glu Val Met Arg Ala Phe Ser
                165                 170                 175

Ser Ser Arg Asn Leu
            180


<210> SEQ ID NO 2
<211> LENGTH: 179
<212> TYPE: PRT
<213> ORGANISM: Sus scrofa

<400> SEQUENCE: 2

Met Ala Pro Thr Ser Ala Phe Leu Thr Ala Leu Val Leu Leu Ser Cys
1               5                   10                  15

Asn Ala Ile Cys Cys Leu Gly Cys Asp Leu Pro Gln Thr His Ser Leu
            20                  25                  30

Ala His Thr Arg Ala Leu Arg Leu Leu Ala Gln Met Arg Arg Ile Ser
        35                  40                  45

Pro Phe Ser Cys Leu Asp His Arg Arg Asp Phe Gly Phe Pro Gln Glu
    50                  55                  60

Ala Leu Gly Gly Asn Gln Val Gln Lys Ala Gln Ala Met Ala Leu Val
65                  70                  75                  80

His Glu Met Leu Gln Gln Thr Phe Gln Leu Phe Ser Thr Glu Gly Ser
                85                  90                  95

Ala Ala Ala Trp Asp Glu Ser Leu Leu His Gln Phe Cys Thr Gly Leu
            100                 105                 110

Asp Gln Gln Leu Arg Asp Leu Glu Ala Cys Val Met Gln Glu Ala Glu
        115                 120                 125
```

-continued

```
Gly Thr Pro Leu Leu Glu Glu Asp Ser Ile Leu Ala Val Arg Lys Tyr
    130                 135                 140

Phe His Arg Leu Thr Leu Tyr Leu Gln Glu Lys Ser Tyr Ser Pro Cys
145                 150                 155                 160

Ala Trp Glu Ile Val Arg Ala Glu Val Met Arg Ala Phe Ser Ser Ser
                165                 170                 175

Arg Asn Leu


<210> SEQ ID NO 3
<211> LENGTH: 179
<212> TYPE: PRT
<213> ORGANISM: Sus scrofa

<400> SEQUENCE: 3

Met Ala Pro Thr Ser Ala Phe Leu Thr Ala Leu Val Leu Leu Ser Cys
1               5                   10                  15

Asn Ala Ile Cys Ser Leu Gly Cys Asp Leu Pro Gln Thr His Ser Leu
            20                  25                  30

Ala His Thr Arg Ala Leu Arg Leu Leu Ala Gln Met Arg Arg Ile Ser
        35                  40                  45

Pro Phe Ser Cys Leu Asp His Arg Arg Asp Phe Gly Phe Pro Gln Glu
    50                  55                  60

Ala Leu Gly Gly Asn Gln Val Gln Lys Ala Gln Ala Met Ala Leu Val
65                  70                  75                  80

His Glu Met Leu Gln Gln Thr Phe Gln Leu Phe Ser Thr Glu Gly Ser
                85                  90                  95

Ala Ala Ala Trp Asp Glu Ser Leu Leu His Gln Phe Cys Thr Gly Leu
            100                 105                 110

Asp Gln Gln Leu Arg Asp Leu Glu Ala Cys Val Met Gln Glu Val Glu
        115                 120                 125

Gly Thr Pro Leu Leu Glu Glu Asp Ser Ile Leu Ala Val Arg Lys Tyr
    130                 135                 140

Phe His Arg Leu Thr Leu Tyr Leu Gln Glu Lys Ser Tyr Ser Pro Cys
145                 150                 155                 160

Ala Trp Glu Ile Val Arg Ala Glu Val Met Arg Ser Phe Ser Ser Ser
                165                 170                 175

Thr Asn Leu


<210> SEQ ID NO 4
<211> LENGTH: 187
<212> TYPE: PRT
<213> ORGANISM: Sus scrofa

<400> SEQUENCE: 4

Met Ala Pro Thr Ser Ala Phe Phe Thr Ala Leu Val Leu Leu Ser Cys
1               5                   10                  15

Asn Ala Ile Cys Ser Leu Gly Cys Asp Leu Pro Gln Thr His Ser Leu
            20                  25                  30

Ala His Thr Arg Ala Leu Arg Leu Leu Ala Gln Met Arg Arg Ile Ser
        35                  40                  45

Pro Phe Ser Cys Leu Asp His Arg Arg Asp Phe Gly Ser Pro His Glu
    50                  55                  60

Ala Leu Gly Gly Asn Gln Val Gln Lys Ala Gln Ala Met Ala Leu Val
65                  70                  75                  80

His Glu Met Leu Gln Gln Thr Phe Gln Leu Phe Ser Thr Glu Gly Ser
                85                  90                  95
```

-continued

```
Ala Ala Ala Trp Asp Glu Ser Leu Leu His Gln Phe Cys Thr Gly Leu
            100                 105                 110

Asp Gln Gln Leu Arg Asp Leu Glu Ala Cys Val Met Gln Glu Val Glu
        115                 120                 125

Gly Thr Pro Leu Leu Glu Glu Asp Ser Ile Leu Ala Val Arg Lys Tyr
    130                 135                 140

Phe His Arg Leu Thr Leu Tyr Leu Gln Glu Lys Ser Tyr Ser Pro Cys
145                 150                 155                 160

Ala Trp Glu Ile Ile Arg Ala Glu Val Met Arg Val Phe Ser Ser Ser
                165                 170                 175

Thr Asn Leu Gln Asp Arg Phe Arg Lys Lys Glu
            180                 185


<210> SEQ ID NO 5
<211> LENGTH: 187
<212> TYPE: PRT
<213> ORGANISM: Sus scrofa

<400> SEQUENCE: 5

Met Ala Pro Thr Ser Ala Phe Leu Thr Ala Leu Val Leu Leu Ser Cys
1               5                   10                  15

Asn Ala Ile Tyr Ser Leu Gly Cys Asp Leu Pro Gln Thr Tyr Ser Leu
            20                  25                  30

Ala His Thr Arg Ala Leu Arg Pro Leu Ala Gln Met Arg Arg Ile Ser
        35                  40                  45

Pro Phe Ser Cys Leu Asp Tyr Arg Arg Asp Phe Gly Phe Pro Gln Glu
    50                  55                  60

Ala Leu Gly Gly Asn Gln Val Gln Lys Ala Gln Ala Met Ala Leu Val
65                  70                  75                  80

His Glu Met Leu Gln Gln Thr Ser Gln Leu Phe Ser Thr Glu Gly Ser
                85                  90                  95

Ala Ala Ala Trp Asp Asp Ser Leu Leu His Gln Phe Cys Thr Gly Leu
            100                 105                 110

Asp Gln Gln Leu Arg Asp Leu Glu Ala Cys Val Met Gln Glu Ala Glu
        115                 120                 125

Gly Thr Pro Leu Leu Glu Glu Asp Ser Ile Leu Ala Val Arg Lys Tyr
    130                 135                 140

Phe His Arg Leu Thr Leu Tyr Leu Gln Glu Lys Ser Tyr Ser Pro Cys
145                 150                 155                 160

Ala Trp Glu Ile Val Arg Ala Glu Val Met Arg Ala Phe Ser Ser Ser
                165                 170                 175

Thr Asn Leu Gln Asp Arg Leu Arg Lys Lys Glu
            180                 185


<210> SEQ ID NO 6
<211> LENGTH: 187
<212> TYPE: PRT
<213> ORGANISM: Sus scrofa

<400> SEQUENCE: 6

Met Ala Pro Thr Ser Ala Phe Leu Thr Ala Leu Val Leu Leu Ser Cys
1               5                   10                  15

Asn Ala Ile Cys Ser Leu Gly Cys Asp Leu Pro Gln Thr His Ser Leu
            20                  25                  30

Ala His Thr Arg Ala Leu Arg Leu Leu Ala Gln Met Arg Arg Ile Ser
        35                  40                  45
```

-continued

```
Pro Phe Ser Cys Leu Asp His Arg Arg Asp Phe Gly Ser Pro His Glu
    50                  55                  60

Ala Phe Gly Gly Asn Gln Val Gln Lys Ala Gln Ala Met Ala Leu Val
65                  70                  75                  80

His Glu Met Leu Gln Gln Thr Phe Gln Leu Phe Ser Thr Glu Gly Ser
                85                  90                  95

Ala Ala Ala Trp Asp Glu Ser Leu Leu His Gln Phe Cys Thr Gly Leu
            100                 105                 110

Asp Gln Gln Leu Arg Asp Leu Glu Ala Cys Val Met Gln Glu Ala Glu
        115                 120                 125

Gly Thr Pro Leu Leu Glu Glu Asp Ser Ile Leu Ala Val Arg Lys Tyr
    130                 135                 140

Phe His Arg Leu Thr Leu Tyr Leu Gln Glu Lys Ser Tyr Ser Pro Cys
145                 150                 155                 160

Ala Trp Glu Ile Val Arg Ala Glu Val Met Arg Ser Phe Ser Ser Ser
                165                 170                 175

Arg Asn Leu Gln Asp Arg Leu Arg Lys Lys Glu
            180                 185


<210> SEQ ID NO 7
<211> LENGTH: 179
<212> TYPE: PRT
<213> ORGANISM: Sus scrofa

<400> SEQUENCE: 7

Met Ala Pro Thr Ser Ala Phe Phe Thr Ala Leu Val Leu Leu Ser Tyr
1               5                   10                  15

Asn Ala Ile Cys Ser Leu Gly Cys Asp Leu Pro Gln Thr His Ser Leu
            20                  25                  30

Ala His Thr Arg Ala Leu Arg Leu Leu Ala Gln Met Arg Arg Ile Ser
        35                  40                  45

Pro Phe Ser Cys Leu Asp His Arg Arg Asp Phe Gly Ser Pro His Glu
    50                  55                  60

Ala Leu Gly Gly Asn Gln Val Gln Lys Ala Gln Ala Met Ala Leu Val
65                  70                  75                  80

His Glu Met Leu Gln Gln Thr Phe Gln Leu Phe Ser Thr Glu Gly Ser
                85                  90                  95

Ala Ala Ala Trp Asn Glu Ser Leu Leu His Gln Phe Cys Thr Gly Leu
            100                 105                 110

Asp Gln Gln Leu Arg Asp Leu Glu Ala Cys Val Met Gln Glu Ala Glu
        115                 120                 125

Gly Thr Pro Leu Leu Glu Glu Asp Ser Ile Leu Ala Val Arg Lys Tyr
    130                 135                 140

Phe His Arg Leu Thr Leu Tyr Leu Gln Glu Lys Ser Tyr Ser Pro Cys
145                 150                 155                 160

Ala Trp Glu Ile Val Arg Ala Glu Val Met Thr Ser Phe Ser Ser Ser
                165                 170                 175

Thr His Leu


<210> SEQ ID NO 8
<211> LENGTH: 187
<212> TYPE: PRT
<213> ORGANISM: Sus scrofa
```

<400> SEQUENCE: 8

```
Met Ala Pro Thr Ser Ala Phe Leu Thr Ala Leu Val Leu Leu Ser Cys
1               5                   10                  15

Asn Ala Ile Cys Ser Leu Gly Cys Asp Leu Pro Gln Thr His Ser Leu
            20                  25                  30

Ala His Thr Arg Ala Leu Arg Leu Leu Ala Gln Met Arg Arg Ile Ser
        35                  40                  45

Pro Phe Ser Cys Leu Asp His Arg Arg Asp Phe Gly Phe Pro Gln Glu
    50                  55                  60

Ala Leu Gly Gly Asn Gln Val Gln Lys Ala Gln Ala Met Ala Leu Val
65                  70                  75                  80

His Glu Met Leu Gln Gln Thr Phe Gln Leu Phe Ser Thr Glu Gly Ser
                85                  90                  95

Ala Ala Ala Trp Asp Glu Ser Leu Leu His Gln Phe Cys Thr Gly Leu
            100                 105                 110

Asp Gln Gln Leu Arg Asp Leu Glu Ala Cys Val Met Gln Glu Ala Glu
        115                 120                 125

Gly Thr Pro Leu Leu Glu Glu Asp Ser Ile Leu Ala Val Arg Lys Tyr
    130                 135                 140

Phe His Arg Leu Thr Leu Tyr Leu Gln Glu Lys Ser Tyr Ser Pro Cys
145                 150                 155                 160

Ala Trp Glu Ile Val Arg Ala Glu Val Met Arg Ala Phe Ser Ser Ser
                165                 170                 175

Thr Asn Leu Gln Asp Arg Leu Arg Arg Lys Glu
            180                 185
```

<210> SEQ ID NO 9
<211> LENGTH: 187
<212> TYPE: PRT
<213> ORGANISM: Sus scrofa

<400> SEQUENCE: 9

```
Met Ala Pro Thr Ser Ala Phe Leu Met Ala Leu Val Leu Leu Ser Cys
1               5                   10                  15

Lys Ala Ile Cys Ser Leu Gly Cys Asp Leu Pro Gln Thr His Ser Leu
            20                  25                  30

Ala His Thr Arg Ala Leu Arg Leu Leu Ala Gln Met Arg Arg Ile Ser
        35                  40                  45

Pro Phe Ser Cys Leu Asp His Arg Arg Asp Phe Gly Phe Pro Gln Glu
    50                  55                  60

Ala Leu Gly Gly Asn Gln Val Gln Lys Ala Gln Ala Met Ala Leu Val
65                  70                  75                  80

His Glu Met Leu Gln Gln Thr Phe Gln Leu Phe Ser Thr Glu Gly Ser
                85                  90                  95

Ala Ala Ala Trp Asn Glu Ser Leu Leu His Gln Phe Cys Thr Gly Leu
            100                 105                 110

Asp Gln Gln Leu Arg Asp Leu Glu Ala Cys Val Met Gln Glu Val Glu
        115                 120                 125

Gly Thr Pro Leu Leu Glu Glu Asp Ser Ile Leu Ala Val Arg Lys Tyr
    130                 135                 140

Phe His Arg Leu Thr Leu Tyr Leu Gln Glu Lys Ser Tyr Ser Pro Cys
145                 150                 155                 160

Ala Trp Glu Ile Val Arg Ala Glu Val Met Arg Ala Phe Ser Ser Ser
                165                 170                 175
```

-continued

```
Thr Asn Leu Gln Asp Arg Leu Arg Lys Lys Glu
            180                 185


<210> SEQ ID NO 10
<211> LENGTH: 179
<212> TYPE: PRT
<213> ORGANISM: Sus scrofa

<400> SEQUENCE: 10

Met Ala Pro Thr Ser Ala Phe Leu Thr Ala Leu Val Leu Leu Ser Cys
1               5                   10                  15

Asn Ala Ile Cys Ser Leu Gly Cys Asn Leu Pro Gln Thr His Ser Leu
            20                  25                  30

Ala His Thr Arg Ala Leu Arg Leu Leu Ala Gln Met Arg Arg Ile Ser
        35                  40                  45

Pro Phe Ser Cys Leu Asp His Arg Lys Asp Phe Gly Phe Pro Gln Glu
    50                  55                  60

Ala Leu Gly Gly Asn Gln Val Gln Lys Ala Gln Ala Met Ala Leu Val
65                  70                  75                  80

His Glu Met Leu Gln Gln Thr Phe Gln Leu Phe Ser Thr Glu Gly Ser
                85                  90                  95

Ala Ala Ala Trp Asn Glu Ser Leu Leu His Gln Phe Cys Thr Gly Leu
            100                 105                 110

Asp Gln Gln Leu Arg Asp Leu Glu Ala Cys Val Met Gln Glu Ala Glu
        115                 120                 125

Gly Thr Pro Leu Leu Glu Glu Asp Ser Ile Leu Ala Val Arg Lys Tyr
    130                 135                 140

Phe His Arg Leu Thr Leu Tyr Leu Gln Glu Lys Ser Tyr Ser Pro Cys
145                 150                 155                 160

Ala Trp Glu Ile Val Arg Ala Glu Val Met Arg Ser Phe Ser Ser Ser
                165                 170                 175

Arg Asn Leu


<210> SEQ ID NO 11
<211> LENGTH: 179
<212> TYPE: PRT
<213> ORGANISM: Sus scrofa

<400> SEQUENCE: 11

Met Ala Pro Thr Ser Ala Phe Phe Thr Ala Leu Val Leu Leu Ser Tyr
1               5                   10                  15

Asn Ala Ile Cys Ser Leu Gly Cys Asp Leu Pro Gln Thr His Ser Leu
            20                  25                  30

Ala His Thr Arg Ala Leu Arg Leu Leu Ala Gln Met Arg Arg Ile Ser
        35                  40                  45

Pro Phe Ser Cys Leu Asp His Arg Arg Asp Phe Gly Ser Pro His Glu
    50                  55                  60

Ala Leu Gly Gly Asn Gln Val Gln Lys Ala Gln Ala Met Ala Leu Val
65                  70                  75                  80

His Glu Met Leu Gln Gln Thr Phe Gln Leu Phe Ser Thr Glu Gly Ser
                85                  90                  95

Ala Ala Ala Trp Asn Glu Ser Leu Leu His Gln Phe Cys Thr Gly Leu
            100                 105                 110

Asp Gln Gln Leu Arg Asp Leu Glu Ala Cys Val Met Gln Glu Ala Glu
        115                 120                 125

Gly Thr Pro Leu Leu Glu Glu Asp Ser Ile Leu Ala Val Arg Lys Tyr
```

```
    130                 135                 140

Phe His Arg Leu Ile Leu Tyr Leu Gln Glu Lys Ser Tyr Ser Pro Cys
145                 150                 155                 160

Ala Trp Glu Ile Val Arg Ala Glu Val Met Thr Ser Phe Ser Ser Ser
                165                 170                 175

Thr His Leu


<210> SEQ ID NO 12
<211> LENGTH: 187
<212> TYPE: PRT
<213> ORGANISM: Sus scrofa

<400> SEQUENCE: 12

Met Ala Pro Thr Ser Ala Phe Leu Thr Val Leu Val Leu Leu Ser Cys
1               5                   10                  15

Asn Ala Ile Cys Cys Leu Gly Cys Asp Leu Pro Gln Thr His Ser Leu
            20                  25                  30

Ala His Thr Arg Ala Leu Arg Leu Leu Ala Gln Met Arg Arg Ile Ser
        35                  40                  45

Pro Phe Ser Cys Leu Asp His Arg Arg Asp Phe Gly Ser Pro His Glu
    50                  55                  60

Ala Phe Gly Gly Asn Gln Val Gln Lys Ala Gln Ala Met Ala Leu Val
65                  70                  75                  80

His Glu Met Leu Gln Gln Thr Phe Gln Leu Phe Ser Thr Glu Gly Ser
                85                  90                  95

Ala Ala Ala Trp Asp Glu Ser Leu Leu His Gln Phe Cys Thr Gly Leu
            100                 105                 110

Asp Gln Gln Leu Arg Asp Leu Glu Ala Cys Val Met Gln Glu Ala Glu
        115                 120                 125

Gly Thr Pro Leu Leu Glu Glu Asp Ser Ile Leu Ala Val Arg Lys Tyr
    130                 135                 140

Phe His Arg Leu Thr Leu Tyr Leu Gln Glu Lys Ser Tyr Ser Pro Cys
145                 150                 155                 160

Ala Trp Glu Ile Val Arg Ala Glu Val Met Arg Val Phe Ser Ser Ser
                165                 170                 175

Thr Asn Leu Gln Asp Arg Leu Arg Lys Lys Glu
            180                 185


<210> SEQ ID NO 13
<211> LENGTH: 187
<212> TYPE: PRT
<213> ORGANISM: Sus scrofa

<400> SEQUENCE: 13

Met Ala Pro Ser Ser Ala Leu Leu Thr Ala Leu Val Leu Leu Ser Cys
1               5                   10                  15

Asn Ala Ile Cys Ser Leu Gly Cys Asn Leu Pro Gln Thr His Ser Leu
            20                  25                  30

Ala His Thr Arg Ala Leu Arg Leu Leu Ala Gln Met Arg Arg Ile Ser
        35                  40                  45

Pro Phe Ser Cys Leu Asp His Arg Arg Asp Phe Gly Ser Pro His Glu
    50                  55                  60

Ala Phe Gly Gly Asn Gln Val Gln Lys Ala Gln Ala Met Ala Leu Val
65                  70                  75                  80

His Glu Met Leu Gln Gln Thr Phe Gln Leu Phe Ser Thr Glu Gly Ser
                85                  90                  95
```

```
Ala Ala Ala Trp Asp Glu Ser Leu Leu His Gln Phe Cys Thr Gly Leu
            100                 105                 110

Asp Gln Gln Leu Arg Asp Leu Glu Ala Cys Val Met Gln Glu Ala Glu
        115                 120                 125

Gly Thr Pro Leu Leu Glu Glu Asp Ser Ile Leu Ala Val Arg Lys Tyr
    130                 135                 140

Phe His Arg Leu Thr Leu Tyr Leu Gln Glu Lys Ser Tyr Ser Pro Cys
145                 150                 155                 160

Ala Trp Glu Ile Val Arg Ala Glu Val Met Arg Ala Phe Ser Ser Ser
                165                 170                 175

Thr Asn Leu Gln Asp Arg Leu Arg Arg Lys Glu
            180                 185


<210> SEQ ID NO 14
<211> LENGTH: 187
<212> TYPE: PRT
<213> ORGANISM: Sus scrofa

<400> SEQUENCE: 14

Met Ala Pro Ser Ser Thr Leu Leu Thr Val Leu Val Leu Leu Ser Cys
1               5                   10                  15

Asn Ala Ile Cys Cys Leu Gly Cys Asn Leu Pro Gln Thr His Ser Leu
            20                  25                  30

Ala His Thr Arg Ala Leu Arg Leu Leu Ala Gln Met Arg Arg Ile Ser
        35                  40                  45

Pro Phe Ser Cys Leu Asp His Arg Arg Asp Phe Gly Ser Pro His Glu
    50                  55                  60

Ala Phe Gly Gly Asn Gln Val Gln Lys Ala Gln Ala Met Ala Leu Val
65                  70                  75                  80

His Glu Met Leu Gln Gln Thr Phe Gln Leu Phe Ser Thr Glu Gly Ser
                85                  90                  95

Ala Ala Ala Trp Asp Glu Ser Leu Leu His Gln Phe Cys Thr Gly Leu
            100                 105                 110

Asp Gln Gln Leu Arg Asp Leu Glu Ala Cys Val Ile Gln Glu Ala Glu
        115                 120                 125

Gly Thr Pro Leu Leu Glu Glu Asp Ser Ile Leu Ala Val Arg Lys Tyr
    130                 135                 140

Phe His Arg Leu Thr Leu Tyr Leu Gln Glu Lys Asn Tyr Ser Leu Cys
145                 150                 155                 160

Ala Trp Glu Ile Ile Arg Ala Glu Val Met Arg Val Phe Ser Ser Ser
                165                 170                 175

Thr Asn Leu Gln Asp Arg Leu Arg Lys Lys Glu
            180                 185


<210> SEQ ID NO 15
<211> LENGTH: 186
<212> TYPE: PRT
<213> ORGANISM: Sus scrofa

<400> SEQUENCE: 15

Met Ala Pro Thr Ser Ala Phe Leu Met Ala Leu Val Leu Leu Ser Cys
1               5                   10                  15

Asn Ala Ile Cys Ser Leu Gly Cys Asp Leu Pro Gln Thr His Ser Leu
            20                  25                  30

Ala His Thr Arg Ala Leu Arg Leu Leu Ala Gln Met Arg Ile Ser Pro
        35                  40                  45
```

-continued

```
Phe Ser Cys Leu Asp His Arg Arg Asp Phe Gly Phe Pro Gln Glu Ala
    50                  55                  60

Leu Gly Gly Asn Gln Val Gln Lys Ala Gln Ala Met Ala Leu Val His
65                  70                  75                  80

Glu Met Leu Gln Gln Thr Phe Gln Leu Phe Ser Thr Glu Gly Ser Ala
                85                  90                  95

Ala Ala Trp Asp Glu Ser Leu Leu His Gln Phe Cys Thr Gly Leu Asp
            100                 105                 110

Gln Gln Leu Arg Asp Leu Glu Ala Cys Val Met Gln Glu Ala Gly Gly
        115                 120                 125

Thr Pro Leu Leu Glu Glu Asp Ser Ile Leu Ala Val Arg Lys Tyr Phe
    130                 135                 140

His Arg Leu Thr Leu Tyr Leu Gln Glu Lys Ser Tyr Ser Pro Cys Ala
145                 150                 155                 160

Trp Glu Ile Val Arg Ala Glu Val Met Arg Ala Phe Ser Ser Ser Thr
                165                 170                 175

Asn Leu Gln Asp Arg Leu Arg Arg Lys Glu
            180                 185


<210> SEQ ID NO 16
<211> LENGTH: 187
<212> TYPE: PRT
<213> ORGANISM: Sus scrofa

<400> SEQUENCE: 16

Met Ala Pro Thr Ser Ala Phe Phe Thr Ala Leu Val Leu Leu Ser Cys
1               5                   10                  15

Asn Ala Ile Cys Ser Leu Gly Cys Asp Pro Val Gln Thr His Ser Leu
            20                  25                  30

Ala His Thr Arg Ala Leu Arg Leu Leu Ala Gln Met Arg Arg Ile Ser
        35                  40                  45

Pro Phe Ser Cys Leu Asp His Arg Arg Asp Phe Gly Phe Pro Gln Glu
    50                  55                  60

Ala Leu Gly Gly Asn Gln Val Gln Lys Ala Gln Ala Met Ala Leu Val
65                  70                  75                  80

His Glu Met Leu Gln Gln Thr Phe Gln Leu Phe Ser Thr Glu Gly Ser
                85                  90                  95

Ala Ala Ala Trp Asp Glu Ser Leu Leu His Gln Phe Cys Thr Gly Leu
            100                 105                 110

Asp Gln Gln Leu Arg Asp Leu Glu Ala Cys Val Met Gln Glu Val Glu
        115                 120                 125

Gly Thr Pro Leu Leu Glu Glu Gly Ser Ile Leu Ala Val Arg Lys Tyr
    130                 135                 140

Phe His Arg Leu Thr Leu Tyr Leu Gln Glu Lys Ser Tyr Ser Pro Cys
145                 150                 155                 160

Ala Trp Glu Ile Ile Arg Ala Glu Val Met Arg Ala Phe Ser Ser Ser
                165                 170                 175

Thr Asn Leu Gln Asp Arg Leu Arg Arg Lys Glu
            180                 185


<210> SEQ ID NO 17
<211> LENGTH: 179
<212> TYPE: PRT
<213> ORGANISM: Sus scrofa

<400> SEQUENCE: 17
```

Met Ala Pro Thr Ser Ala Phe Phe Thr Ala Leu Val Leu Leu Ser Cys
1 5 10 15

Asn Ala Ile Cys Ser Leu Gly Cys Asp Leu Pro Gln Thr His Ser Leu
20 25 30

Ala His Thr Arg Ala Leu Arg Leu Leu Ala Gln Met Arg Arg Ile Ser
35 40 45

Pro Phe Ser Cys Leu Asp His Arg Arg Asp Phe Gly Phe Pro Gln Glu
50 55 60

Ala Leu Gly Gly Asn Gln Val Gln Lys Ala Gln Ala Met Ala Leu Val
65 70 75 80

His Glu Met Leu Gln Gln Thr Phe Gln Leu Phe Ser Thr Glu Gly Ser
85 90 95

Ala Ala Ala Trp Asp Glu Ser Leu Leu His Gln Phe Cys Thr Gly Leu
100 105 110

Asp Gln Gln Leu Arg Asp Leu Glu Ala Cys Val Met Gln Glu Val Glu
115 120 125

Gly Thr Pro Leu Leu Glu Glu Asp Ser Ile Leu Ala Val Arg Lys Tyr
130 135 140

Phe His Arg Leu Thr Leu Tyr Leu Gln Glu Lys Ser Tyr Ser Pro Cys
145 150 155 160

Ala Trp Glu Ile Val Arg Ala Glu Val Met Arg Ala Phe Ser Ser Ser
165 170 175

Arg Asn Leu

<210> SEQ ID NO 18
<211> LENGTH: 228
<212> TYPE: PRT
<213> ORGANISM: Sus scrofa

<400> SEQUENCE: 18

Gly Thr Lys Thr Lys Pro Pro Cys Pro Ile Cys Pro Gly Cys Glu Val
1 5 10 15

Ala Gly Pro Ser Val Phe Ile Phe Pro Pro Lys Pro Lys Asp Thr Leu
20 25 30

Met Ile Ser Gln Thr Pro Glu Val Thr Cys Val Val Val Asp Val Ser
35 40 45

Lys Glu His Ala Glu Val Gln Phe Ser Trp Tyr Val Asp Gly Val Glu
50 55 60

Val His Thr Ala Glu Thr Arg Pro Lys Glu Glu Gln Phe Asn Ser Thr
65 70 75 80

Tyr Arg Val Val Ser Val Leu Pro Ile Gln His Gln Asp Trp Leu Lys
85 90 95

Gly Lys Glu Phe Lys Cys Lys Val Asn Asn Val Asp Leu Pro Ala Pro
100 105 110

Ile Thr Arg Thr Ile Ser Lys Ala Ile Gly Gln Ser Arg Glu Pro Tyr
115 120 125

Thr Leu Pro Pro Pro Ala Glu Glu Leu Ser Arg Ser Lys Val Thr Val
130 135 140

Thr Cys Leu Val Ile Gly Phe Tyr Pro Pro Asp Ile His Val Glu Trp
145 150 155 160

Lys Ser Asn Gly Gln Pro Glu Pro Glu Gly Asn Tyr Arg Thr Thr Pro
165 170 175

Pro Gln Gln Asp Val Asp Gly Thr Phe Phe Leu Tyr Ser Lys Leu Ala
180 185 190

-continued

Val Asp Lys Ala Arg Trp Asp His Gly Glu Thr Phe Glu Cys Ala Val
195 200 205

Met His Glu Ala Leu His Asn His Tyr Thr Gln Lys Ser Ile Ser Lys
210 215 220

Thr Gln Gly Lys
225

<210> SEQ ID NO 19
<211> LENGTH: 228
<212> TYPE: PRT
<213> ORGANISM: Sus scrofa

<400> SEQUENCE: 19

Gly Ile His Gln Pro Gln Thr Cys Pro Ile Cys Pro Gly Cys Glu Val
1 5 10 15

Ala Gly Pro Ser Val Phe Ile Phe Pro Pro Lys Pro Lys Asp Thr Leu
20 25 30

Met Ile Ser Gln Thr Pro Glu Val Thr Cys Val Val Val Asp Val Ser
35 40 45

Lys Glu His Ala Glu Val Gln Phe Ser Trp Tyr Val Asp Gly Val Glu
50 55 60

Val His Thr Ala Glu Thr Arg Pro Lys Glu Glu Gln Phe Asn Ser Thr
65 70 75 80

Tyr Arg Val Val Ser Val Leu Pro Ile Gln His Gln Asp Trp Leu Lys
85 90 95

Gly Lys Glu Phe Lys Cys Lys Val Asn Asn Val Asp Leu Pro Ala Pro
100 105 110

Ile Thr Arg Thr Ile Ser Lys Ala Ile Gly Gln Ser Arg Glu Pro Tyr
115 120 125

Thr Leu Pro Pro Pro Ala Glu Glu Leu Ser Arg Ser Lys Val Thr Leu
130 135 140

Thr Cys Leu Val Ile Gly Phe Tyr Pro Pro Asp Ile His Val Glu Trp
145 150 155 160

Lys Ser Asn Gly Gln Pro Glu Pro Glu Asn Thr Tyr Arg Thr Thr Pro
165 170 175

Pro Gln Gln Asp Val Asp Gly Thr Phe Phe Leu Tyr Ser Lys Leu Ala
180 185 190

Val Asp Lys Ala Arg Trp Asp His Gly Asp Lys Phe Glu Cys Ala Val
195 200 205

Met His Glu Ala Leu His Asn His Tyr Thr Gln Lys Ser Ile Ser Lys
210 215 220

Thr Gln Gly Lys
225

<210> SEQ ID NO 20
<211> LENGTH: 228
<212> TYPE: PRT
<213> ORGANISM: Sus scrofa

<400> SEQUENCE: 20

Gly Thr Lys Thr Lys Pro Pro Cys Pro Ile Cys Pro Ala Cys Glu Ser
1 5 10 15

Pro Gly Pro Ser Val Phe Ile Phe Pro Pro Lys Pro Lys Asp Thr Leu
20 25 30

Met Ile Ser Arg Thr Pro Gln Val Thr Cys Val Val Val Asp Val Ser
35 40 45

-continued

```
Gln Glu Asn Pro Glu Val Gln Phe Ser Trp Tyr Val Asp Gly Val Glu
    50                  55                  60

Val His Thr Ala Gln Thr Arg Pro Lys Glu Glu Gln Phe Asn Ser Thr
65                  70                  75                  80

Tyr Arg Val Val Ser Val Leu Pro Ile Gln His Gln Asp Trp Leu Asn
                85                  90                  95

Gly Lys Glu Phe Lys Cys Lys Val Asn Asn Lys Asp Leu Pro Ala Pro
            100                 105                 110

Ile Thr Arg Ile Ile Ser Lys Ala Lys Gly Gln Thr Arg Glu Pro Tyr
        115                 120                 125

Thr Leu Pro Pro His Ala Glu Glu Leu Ser Arg Ser Lys Val Ser Ile
    130                 135                 140

Thr Cys Leu Val Ile Gly Phe Tyr Pro Pro Asp Ile Asp Val Glu Trp
145                 150                 155                 160

Gln Arg Asn Gly Gln Pro Glu Pro Glu Gly Asn Tyr Arg Thr Thr Pro
                165                 170                 175

Pro Gln Gln Asp Val Asp Gly Thr Tyr Phe Leu Tyr Ser Lys Phe Ser
            180                 185                 190

Val Asp Lys Ala Ser Trp Gln Gly Gly Gly Ile Phe Gln Cys Ala Val
        195                 200                 205

Met His Glu Ala Leu His Asn His Tyr Thr Gln Lys Ser Ile Ser Lys
    210                 215                 220

Thr Pro Gly Lys
225


<210> SEQ ID NO 21
<211> LENGTH: 228
<212> TYPE: PRT
<213> ORGANISM: Sus scrofa

<400> SEQUENCE: 21

Gly Thr Lys Thr Lys Pro Pro Cys Pro Ile Cys Pro Ala Cys Glu Ser
1               5                   10                  15

Pro Gly Pro Ser Val Phe Ile Phe Pro Pro Lys Pro Lys Asp Thr Leu
            20                  25                  30

Met Ile Ser Arg Thr Pro Gln Val Thr Cys Val Val Val Asp Val Ser
        35                  40                  45

Gln Glu Asn Pro Glu Val Gln Phe Ser Trp Tyr Val Asp Gly Val Glu
    50                  55                  60

Val His Thr Ala Gln Thr Arg Pro Lys Glu Glu Gln Phe Asn Ser Thr
65                  70                  75                  80

Tyr Arg Val Val Ser Val Leu Pro Ile Gln His Gln Asp Trp Leu Asn
                85                  90                  95

Gly Lys Glu Phe Lys Cys Lys Val Asn Asn Lys Asp Leu Pro Ala Pro
            100                 105                 110

Ile Thr Arg Ile Ile Ser Lys Ala Lys Gly Gln Thr Arg Glu Pro Tyr
        115                 120                 125

Thr Leu Pro Pro His Ala Glu Glu Leu Ser Arg Ser Lys Val Ser Ile
    130                 135                 140

Thr Cys Leu Val Ile Gly Phe Tyr Pro Pro Asp Ile Asp Val Glu Trp
145                 150                 155                 160

Gln Arg Asn Gly Gln Pro Glu Pro Glu Gly Asn Tyr Arg Thr Thr Pro
                165                 170                 175

Pro Gln Gln Asp Val Asp Gly Thr Tyr Phe Leu Tyr Ser Lys Phe Ser
```

-continued

```
            180                 185                 190

Val Asp Lys Ala Ser Trp Gln Gly Gly Gly Ile Phe Gln Cys Ala Val
        195                 200                 205

Met His Glu Ala Leu His Asn His Tyr Thr Gln Lys Ser Ile Ser Lys
    210                 215                 220

Thr Pro Gly Lys
225


<210> SEQ ID NO 22
<211> LENGTH: 230
<212> TYPE: PRT
<213> ORGANISM: Sus scrofa

<400> SEQUENCE: 22

Gly Thr Lys Thr Lys Pro Pro Cys Pro Ile Cys Pro Ala Cys Glu Gly
1               5                   10                  15

Pro Gly Pro Ser Ala Phe Ile Phe Pro Pro Lys Pro Lys Asp Thr Leu
            20                  25                  30

Met Ile Ser Arg Thr Pro Lys Val Thr Cys Val Val Val Asp Val Ser
        35                  40                  45

Gln Glu Asn Pro Glu Val Gln Phe Ser Trp Tyr Val Asp Gly Val Glu
    50                  55                  60

Val His Thr Ala Gln Thr Arg Pro Lys Glu Glu Gln Phe Asn Ser Thr
65                  70                  75                  80

Tyr Arg Val Val Ser Val Leu Pro Ile Gln His Gln Asp Trp Leu Asn
                85                  90                  95

Gly Lys Glu Phe Lys Cys Lys Val Asn Asn Lys Asp Leu Pro Ala Pro
            100                 105                 110

Ile Thr Arg Ile Ile Ser Lys Ala Lys Gly Gln Thr Arg Glu Pro Gln
        115                 120                 125

Val Tyr Thr Leu Pro Pro Pro Thr Glu Glu Leu Ser Arg Ser Lys Val
    130                 135                 140

Thr Leu Thr Cys Leu Val Thr Gly Phe Tyr Pro Pro Asp Ile Asp Val
145                 150                 155                 160

Glu Trp Gln Arg Asn Gly Gln Pro Glu Pro Glu Gly Asn Tyr Arg Thr
                165                 170                 175

Thr Pro Pro Gln Gln Asp Val Asp Gly Thr Tyr Phe Leu Tyr Ser Lys
            180                 185                 190

Leu Ala Val Asp Lys Ala Ser Trp Gln Arg Gly Asp Thr Phe Gln Cys
        195                 200                 205

Ala Val Met His Glu Ala Leu His Asn His Tyr Thr Gln Lys Ser Ile
    210                 215                 220

Phe Lys Thr Pro Gly Lys
225                 230


<210> SEQ ID NO 23
<211> LENGTH: 16
<212> TYPE: PRT
<213> ORGANISM: Artificial Sequence
<220> FEATURE:
<223> OTHER INFORMATION: Amino acid sequence of a linker of interferon
      and IgG Fc fragment

<400> SEQUENCE: 23

Gly Gly Ser Gly Gly Ser Gly Gly Gly Gly Ser Gly Gly Gly Gly Ser
1               5                   10                  15
```

-continued

```
<210> SEQ ID NO 24
<211> LENGTH: 14
<212> TYPE: PRT
<213> ORGANISM: Artificial Sequence
<220> FEATURE:
<223> OTHER INFORMATION: Amino acid sequence of linker for PMT B-cell
      epitopes

<400> SEQUENCE: 24

Gly Ser Gly Gly Gly Gly Ser Gly Gly Gly Gly Ser Gly Ser
1               5                   10


<210> SEQ ID NO 25
<211> LENGTH: 6
<212> TYPE: PRT
<213> ORGANISM: Artificial Sequence
<220> FEATURE:
<223> OTHER INFORMATION: Amino acid sequence of (GS)3 linker

<400> SEQUENCE: 25

Gly Ser Gly Ser Gly Ser
1               5


<210> SEQ ID NO 26
<211> LENGTH: 15
<212> TYPE: PRT
<213> ORGANISM: Artificial Sequence
<220> FEATURE:
<223> OTHER INFORMATION: amino acid sequence of (GGGGS)3 linker

<400> SEQUENCE: 26

Gly Gly Gly Gly Ser Gly Gly Gly Gly Ser Gly Gly Gly Gly Ser
1               5                   10                  15


<210> SEQ ID NO 27
<211> LENGTH: 4
<212> TYPE: PRT
<213> ORGANISM: Artificial Sequence
<220> FEATURE:
<223> OTHER INFORMATION: amino acid sequence of GGSG linker

<400> SEQUENCE: 27

Gly Gly Ser Gly
1


<210> SEQ ID NO 28
<211> LENGTH: 8
<212> TYPE: PRT
<213> ORGANISM: Artificial Sequence
<220> FEATURE:
<223> OTHER INFORMATION: Amino acid sequence of (GGSG)2 linker

<400> SEQUENCE: 28

Gly Gly Ser Gly Gly Gly Ser Gly
1               5


<210> SEQ ID NO 29
<211> LENGTH: 12
<212> TYPE: PRT
<213> ORGANISM: Artificial Sequence
<220> FEATURE:
<223> OTHER INFORMATION: amino acid sequence of (GGSG)3 linker

<400> SEQUENCE: 29

Gly Gly Ser Gly Gly Gly Ser Gly Gly Gly Ser Gly
1               5                   10
```

-continued

<210> SEQ ID NO 30
<211> LENGTH: 10
<212> TYPE: PRT
<213> ORGANISM: Artificial Sequence
<220> FEATURE:
<223> OTHER INFORMATION: amino acid sequence of GENLYFQSGG linker

<400> SEQUENCE: 30

```
Gly Glu Asn Leu Tyr Phe Gln Ser Gly Gly
1               5                   10
```

<210> SEQ ID NO 31
<211> LENGTH: 36
<212> TYPE: PRT
<213> ORGANISM: Artificial Sequence
<220> FEATURE:
<223> OTHER INFORMATION: amino acid sequence of GAST linker

<400> SEQUENCE: 31

```
Gly Gly Ser Ala Gly Gly Ser Gly Ser Gly Ser Ser Gly Gly Ser Ser
1               5                   10                  15

Gly Ala Ser Gly Thr Gly Thr Ala Gly Gly Thr Gly Ser Gly Ser Gly
            20                  25                  30

Thr Gly Ser Gly
        35
```

<210> SEQ ID NO 32
<211> LENGTH: 36
<212> TYPE: PRT
<213> ORGANISM: Artificial Sequence
<220> FEATURE:
<223> OTHER INFORMATION: amino acid sequence of SEG linker

<400> SEQUENCE: 32

```
Gly Gly Ser Gly Gly Gly Ser Glu Gly Gly Gly Ser Glu Gly Gly Gly
1               5                   10                  15

Ser Glu Gly Gly Gly Ser Glu Gly Gly Gly Ser Glu Gly Gly Gly Ser
            20                  25                  30

Gly Gly Gly Ser
        35
```

<210> SEQ ID NO 33
<211> LENGTH: 26
<212> TYPE: PRT
<213> ORGANISM: Artificial Sequence
<220> FEATURE:
<223> OTHER INFORMATION: Amino acid sequence of (GGS)2(GGGGS)4 linker

<400> SEQUENCE: 33

```
Gly Gly Ser Gly Gly Ser Gly Gly Gly Gly Ser Gly Gly Gly Gly Ser
1               5                   10                  15

Gly Gly Gly Gly Ser Gly Gly Gly Gly Ser
            20                  25
```

<210> SEQ ID NO 34
<211> LENGTH: 27
<212> TYPE: DNA
<213> ORGANISM: Artificial Sequence
<220> FEATURE:
<223> OTHER INFORMATION: Forward primer for interferon

<400> SEQUENCE: 34

```
cccaagctta tggccccaac ctcagcc                                         27
```

<210> SEQ ID NO 35
<211> LENGTH: 27
<212> TYPE: DNA
<213> ORGANISM: Artificial Sequence
<220> FEATURE:
<223> OTHER INFORMATION: Reverse primer for interferon

<400> SEQUENCE: 35
ccgctcgagc aggtttctgg aggaaga 27

<210> SEQ ID NO 36
<211> LENGTH: 21
<212> TYPE: DNA
<213> ORGANISM: Artificial Sequence
<220> FEATURE:
<223> OTHER INFORMATION: Forward primer for IgG Fc fragment

<400> SEQUENCE: 36
cgggatccgg gaacaaagac c 21

<210> SEQ ID NO 37
<211> LENGTH: 22
<212> TYPE: DNA
<213> ORGANISM: Artificial Sequence
<220> FEATURE:
<223> OTHER INFORMATION: Reverse primer for IgG Fc fragment

<400> SEQUENCE: 37
cccaagcttt ttacccggag tc 22

<210> SEQ ID NO 38
<211> LENGTH: 407
<212> TYPE: PRT
<213> ORGANISM: Artificial Sequence
<220> FEATURE:
<223> OTHER INFORMATION: Amino acid sequence of interferon recombinant protein

<400> SEQUENCE: 38

```
Met Ala Pro Thr Ser Ala Phe Leu Thr Ala Leu Val Leu Leu Ser Cys
1               5                   10                  15

Asn Ala Ile Cys Cys Leu Gly Cys Asp Leu Pro Gln Thr His Ser Leu
            20                  25                  30

Ala His Thr Arg Ala Leu Arg Leu Leu Ala Gln Met Arg Arg Ile Ser
        35                  40                  45

Pro Phe Ser Cys Leu Asp His Arg Arg Asp Phe Gly Phe Pro Gln Glu
    50                  55                  60

Ala Leu Gly Gly Asn Gln Val Gln Lys Ala Gln Ala Met Ala Leu Val
65                  70                  75                  80

His Glu Met Leu Gln Gln Thr Phe Gln Leu Phe Ser Thr Glu Gly Ser
                85                  90                  95

Ala Ala Ala Trp Asp Glu Ser Leu Leu His Gln Phe Cys Thr Gly Leu
            100                 105                 110

Asp Gln Gln Leu Arg Asp Leu Glu Ala Cys Val Met Gln Glu Ala Glu
        115                 120                 125

Gly Thr Pro Leu Leu Glu Glu Asp Ser Ile Leu Ala Val Arg Lys Tyr
    130                 135                 140

Phe His Arg Leu Thr Leu Tyr Leu Gln Glu Lys Ser Tyr Ser Pro Cys
145                 150                 155                 160

Ala Trp Glu Ile Val Arg Ala Glu Val Met Arg Ala Phe Ser Ser Ser
                165                 170                 175
```

```
Arg Asn Leu Gly Thr Lys Thr Lys Pro Pro Cys Pro Ile Cys Pro Ala
            180                 185                 190

Cys Glu Gly Pro Gly Pro Ser Ala Phe Ile Phe Pro Pro Lys Pro Lys
        195                 200                 205

Asp Thr Leu Met Ile Ser Arg Thr Pro Lys Val Thr Cys Val Val Val
    210                 215                 220

Asp Val Ser Gln Glu Asn Pro Glu Val Gln Phe Ser Trp Tyr Val Asp
225                 230                 235                 240

Gly Val Glu Val His Thr Ala Gln Thr Arg Pro Lys Glu Glu Gln Phe
                245                 250                 255

Asn Ser Thr Tyr Arg Val Val Ser Val Leu Pro Ile Gln His Gln Asp
            260                 265                 270

Trp Leu Asn Gly Lys Glu Phe Lys Cys Lys Val Asn Asn Lys Asp Leu
        275                 280                 285

Pro Ala Pro Ile Thr Arg Ile Ile Ser Lys Ala Lys Gly Gln Thr Arg
    290                 295                 300

Glu Pro Tyr Thr Leu Pro Pro Pro Thr Glu Glu Leu Ser Arg Ser Lys
305                 310                 315                 320

Val Thr Leu Thr Cys Leu Val Thr Gly Phe Tyr Pro Pro Asp Ile Asp
                325                 330                 335

Val Glu Trp Gln Arg Asn Gly Gln Pro Glu Pro Glu Gly Asn Tyr Arg
            340                 345                 350

Thr Thr Pro Pro Gln Gln Asp Val Asp Gly Thr Tyr Phe Leu Tyr Ser
        355                 360                 365

Lys Leu Ala Val Asp Lys Ala Ser Trp Gln Arg Gly Asp Thr Phe Gln
    370                 375                 380

Cys Ala Val Met His Glu Ala Leu His Asn His Tyr Thr Gln Lys Ser
385                 390                 395                 400

Ile Phe Lys Thr Pro Gly Lys
                405


<210> SEQ ID NO 39
<211> LENGTH: 409
<212> TYPE: PRT
<213> ORGANISM: Artificial Sequence
<220> FEATURE:
<223> OTHER INFORMATION: Amino acid sequence of interferon recombinant
      protein

<400> SEQUENCE: 39

Met Ala Pro Thr Ser Ala Phe Leu Thr Ala Leu Val Leu Leu Ser Cys
1               5                   10                  15

Asn Ala Ile Cys Cys Leu Gly Cys Asp Leu Pro Gln Thr His Ser Leu
            20                  25                  30

Ala His Thr Arg Ala Leu Arg Leu Leu Ala Gln Met Arg Arg Ile Ser
        35                  40                  45

Pro Phe Ser Cys Leu Asp His Arg Arg Asp Phe Gly Phe Pro Gln Glu
    50                  55                  60

Ala Leu Gly Gly Asn Gln Val Gln Lys Ala Gln Ala Met Ala Leu Val
65                  70                  75                  80

His Glu Met Leu Gln Gln Thr Phe Gln Leu Phe Ser Thr Glu Gly Ser
                85                  90                  95

Ala Ala Ala Trp Asp Glu Ser Leu Leu His Gln Phe Cys Thr Gly Leu
            100                 105                 110

Asp Gln Gln Leu Arg Asp Leu Glu Ala Cys Val Met Gln Glu Ala Glu
        115                 120                 125
```

```
Gly Thr Pro Leu Leu Glu Glu Asp Ser Ile Leu Ala Val Arg Lys Tyr
    130                 135                 140

Phe His Arg Leu Thr Leu Tyr Leu Gln Glu Lys Ser Tyr Ser Pro Cys
145                 150                 155                 160

Ala Trp Glu Ile Val Arg Ala Glu Val Met Arg Ala Phe Ser Ser Ser
                165                 170                 175

Arg Asn Leu Gly Gly Gly Thr Lys Thr Lys Pro Pro Cys Pro Ile Cys
            180                 185                 190

Pro Ala Cys Glu Gly Pro Gly Pro Ser Ala Phe Ile Phe Pro Pro Lys
        195                 200                 205

Pro Lys Asp Thr Leu Met Ile Ser Arg Thr Pro Lys Val Thr Cys Val
    210                 215                 220

Val Val Asp Val Ser Gln Glu Asn Pro Glu Val Gln Phe Ser Trp Tyr
225                 230                 235                 240

Val Asp Gly Val Glu Val His Thr Ala Gln Thr Arg Pro Lys Glu Glu
                245                 250                 255

Gln Phe Asn Ser Thr Tyr Arg Val Val Ser Val Leu Pro Ile Gln His
            260                 265                 270

Gln Asp Trp Leu Asn Gly Lys Glu Phe Lys Cys Lys Val Asn Asn Lys
        275                 280                 285

Asp Leu Pro Ala Pro Ile Thr Arg Ile Ile Ser Lys Ala Lys Gly Gln
    290                 295                 300

Thr Arg Glu Pro Tyr Thr Leu Pro Pro Pro Thr Glu Glu Leu Ser Arg
305                 310                 315                 320

Ser Lys Val Thr Leu Thr Cys Leu Val Thr Gly Phe Tyr Pro Pro Asp
                325                 330                 335

Ile Asp Val Glu Trp Gln Arg Asn Gly Gln Pro Glu Pro Glu Gly Asn
            340                 345                 350

Tyr Arg Thr Thr Pro Pro Gln Gln Asp Val Asp Gly Thr Tyr Phe Leu
        355                 360                 365

Tyr Ser Lys Leu Ala Val Asp Lys Ala Ser Trp Gln Arg Gly Asp Thr
    370                 375                 380

Phe Gln Cys Ala Val Met His Glu Ala Leu His Asn His Tyr Thr Gln
385                 390                 395                 400

Lys Ser Ile Phe Lys Thr Pro Gly Lys
                405


<210> SEQ ID NO 40
<211> LENGTH: 409
<212> TYPE: PRT
<213> ORGANISM: Artificial Sequence
<220> FEATURE:
<223> OTHER INFORMATION: Amino acid sequence of interferon recombinant
      protein

<400> SEQUENCE: 40

Met Ala Pro Thr Ser Ala Phe Leu Thr Ala Leu Val Leu Leu Ser Cys
1               5                   10                  15

Asn Ala Ile Cys Cys Leu Gly Cys Asp Leu Pro Gln Thr His Ser Leu
            20                  25                  30

Ala His Thr Arg Ala Leu Arg Leu Leu Ala Gln Met Arg Arg Ile Ser
        35                  40                  45

Pro Phe Ser Cys Leu Asp His Arg Arg Asp Phe Gly Phe Pro Gln Glu
    50                  55                  60

Ala Leu Gly Gly Asn Gln Val Gln Lys Ala Gln Ala Met Ala Leu Val
```

-continued

```
65                  70                  75                  80

His Glu Met Leu Gln Gln Thr Phe Gln Leu Phe Ser Thr Glu Gly Ser
                85                  90                  95

Ala Ala Ala Trp Asp Glu Ser Leu Leu His Gln Phe Cys Thr Gly Leu
            100                 105                 110

Asp Gln Gln Leu Arg Asp Leu Glu Ala Cys Val Met Gln Glu Ala Glu
        115                 120                 125

Gly Thr Pro Leu Leu Glu Glu Asp Ser Ile Leu Ala Val Arg Lys Tyr
    130                 135                 140

Phe His Arg Leu Thr Leu Tyr Leu Gln Glu Lys Ser Tyr Ser Pro Cys
145                 150                 155                 160

Ala Trp Glu Ile Val Arg Ala Glu Val Met Arg Ala Phe Ser Ser Ser
                165                 170                 175

Arg Asn Leu Gly Ser Gly Thr Lys Thr Lys Pro Pro Cys Pro Ile Cys
            180                 185                 190

Pro Ala Cys Glu Gly Pro Gly Pro Ser Ala Phe Ile Phe Pro Pro Lys
        195                 200                 205

Pro Lys Asp Thr Leu Met Ile Ser Arg Thr Pro Lys Val Thr Cys Val
    210                 215                 220

Val Val Asp Val Ser Gln Glu Asn Pro Glu Val Gln Phe Ser Trp Tyr
225                 230                 235                 240

Val Asp Gly Val Glu Val His Thr Ala Gln Thr Arg Pro Lys Glu Glu
                245                 250                 255

Gln Phe Asn Ser Thr Tyr Arg Val Val Ser Val Leu Pro Ile Gln His
            260                 265                 270

Gln Asp Trp Leu Asn Gly Lys Glu Phe Lys Cys Lys Val Asn Asn Lys
        275                 280                 285

Asp Leu Pro Ala Pro Ile Thr Arg Ile Ile Ser Lys Ala Lys Gly Gln
    290                 295                 300

Thr Arg Glu Pro Tyr Thr Leu Pro Pro Pro Thr Glu Glu Leu Ser Arg
305                 310                 315                 320

Ser Lys Val Thr Leu Thr Cys Leu Val Thr Gly Phe Tyr Pro Pro Asp
                325                 330                 335

Ile Asp Val Glu Trp Gln Arg Asn Gly Gln Pro Glu Pro Glu Gly Asn
            340                 345                 350

Tyr Arg Thr Thr Pro Pro Gln Gln Asp Val Asp Gly Thr Tyr Phe Leu
        355                 360                 365

Tyr Ser Lys Leu Ala Val Asp Lys Ala Ser Trp Gln Arg Gly Asp Thr
    370                 375                 380

Phe Gln Cys Ala Val Met His Glu Ala Leu His Asn His Tyr Thr Gln
385                 390                 395                 400

Lys Ser Ile Phe Lys Thr Pro Gly Lys
                405


<210> SEQ ID NO 41
<211> LENGTH: 423
<212> TYPE: PRT
<213> ORGANISM: Artificial Sequence
<220> FEATURE:
<223> OTHER INFORMATION: Amino acid sequence of interferon recombinant
      protein

<400> SEQUENCE: 41

Met Ala Pro Thr Ser Ala Phe Leu Thr Ala Leu Val Leu Leu Ser Cys
1               5                   10                  15
```

-continued

```
Asn Ala Ile Cys Cys Leu Gly Cys Asp Leu Pro Gln Thr His Ser Leu
            20                  25                  30

Ala His Thr Arg Ala Leu Arg Leu Leu Ala Gln Met Arg Arg Ile Ser
        35                  40                  45

Pro Phe Ser Cys Leu Asp His Arg Arg Asp Phe Gly Phe Pro Gln Glu
    50                  55                  60

Ala Leu Gly Gly Asn Gln Val Gln Lys Ala Gln Ala Met Ala Leu Val
65                  70                  75                  80

His Glu Met Leu Gln Gln Thr Phe Gln Leu Phe Ser Thr Glu Gly Ser
                85                  90                  95

Ala Ala Ala Trp Asp Glu Ser Leu Leu His Gln Phe Cys Thr Gly Leu
            100                 105                 110

Asp Gln Gln Leu Arg Asp Leu Glu Ala Cys Val Met Gln Glu Ala Glu
        115                 120                 125

Gly Thr Pro Leu Leu Glu Glu Asp Ser Ile Leu Ala Val Arg Lys Tyr
    130                 135                 140

Phe His Arg Leu Thr Leu Tyr Leu Gln Glu Lys Ser Tyr Ser Pro Cys
145                 150                 155                 160

Ala Trp Glu Ile Val Arg Ala Glu Val Met Arg Ala Phe Ser Ser Ser
                165                 170                 175

Arg Asn Leu Gly Gly Ser Gly Gly Ser Gly Gly Gly Gly Ser Gly Gly
            180                 185                 190

Gly Gly Ser Gly Thr Lys Thr Lys Pro Pro Cys Pro Ile Cys Pro Ala
        195                 200                 205

Cys Glu Gly Pro Gly Pro Ser Ala Phe Ile Phe Pro Pro Lys Pro Lys
    210                 215                 220

Asp Thr Leu Met Ile Ser Arg Thr Pro Lys Val Thr Cys Val Val Val
225                 230                 235                 240

Asp Val Ser Gln Glu Asn Pro Glu Val Gln Phe Ser Trp Tyr Val Asp
                245                 250                 255

Gly Val Glu Val His Thr Ala Gln Thr Arg Pro Lys Glu Glu Gln Phe
            260                 265                 270

Asn Ser Thr Tyr Arg Val Val Ser Val Leu Pro Ile Gln His Gln Asp
        275                 280                 285

Trp Leu Asn Gly Lys Glu Phe Lys Cys Lys Val Asn Asn Lys Asp Leu
    290                 295                 300

Pro Ala Pro Ile Thr Arg Ile Ile Ser Lys Ala Lys Gly Gln Thr Arg
305                 310                 315                 320

Glu Pro Tyr Thr Leu Pro Pro Pro Thr Glu Glu Leu Ser Arg Ser Lys
                325                 330                 335

Val Thr Leu Thr Cys Leu Val Thr Gly Phe Tyr Pro Pro Asp Ile Asp
            340                 345                 350

Val Glu Trp Gln Arg Asn Gly Gln Pro Glu Pro Glu Gly Asn Tyr Arg
        355                 360                 365

Thr Thr Pro Pro Gln Gln Asp Val Asp Gly Thr Tyr Phe Leu Tyr Ser
    370                 375                 380

Lys Leu Ala Val Asp Lys Ala Ser Trp Gln Arg Gly Asp Thr Phe Gln
385                 390                 395                 400

Cys Ala Val Met His Glu Ala Leu His Asn His Tyr Thr Gln Lys Ser
                405                 410                 415

Ile Phe Lys Thr Pro Gly Lys
            420
```

-continued

<210> SEQ ID NO 42
<211> LENGTH: 421
<212> TYPE: PRT
<213> ORGANISM: Artificial Sequence
<220> FEATURE:
<223> OTHER INFORMATION: Amino acid sequence of interferon recombinant protein

<400> SEQUENCE: 42

```
Met Ala Pro Thr Ser Ala Phe Leu Thr Ala Leu Val Leu Leu Ser Cys
1               5                   10                  15

Asn Ala Ile Cys Cys Leu Gly Cys Asp Leu Pro Gln Thr His Ser Leu
            20                  25                  30

Ala His Thr Arg Ala Leu Arg Leu Leu Ala Gln Met Arg Arg Ile Ser
        35                  40                  45

Pro Phe Ser Cys Leu Asp His Arg Arg Asp Phe Gly Phe Pro Gln Glu
    50                  55                  60

Ala Leu Gly Gly Asn Gln Val Gln Lys Ala Gln Ala Met Ala Leu Val
65                  70                  75                  80

His Glu Met Leu Gln Gln Thr Phe Gln Leu Phe Ser Thr Glu Gly Ser
                85                  90                  95

Ala Ala Ala Trp Asp Glu Ser Leu Leu His Gln Phe Cys Thr Gly Leu
            100                 105                 110

Asp Gln Gln Leu Arg Asp Leu Glu Ala Cys Val Met Gln Glu Ala Glu
        115                 120                 125

Gly Thr Pro Leu Leu Glu Glu Asp Ser Ile Leu Ala Val Arg Lys Tyr
    130                 135                 140

Phe His Arg Leu Thr Leu Tyr Leu Gln Glu Lys Ser Tyr Ser Pro Cys
145                 150                 155                 160

Ala Trp Glu Ile Val Arg Ala Glu Val Met Arg Ala Phe Ser Ser Ser
                165                 170                 175

Arg Asn Leu Gly Ser Gly Gly Gly Gly Ser Gly Gly Gly Gly Ser Gly
            180                 185                 190

Ser Gly Thr Lys Thr Lys Pro Pro Cys Pro Ile Cys Pro Ala Cys Glu
        195                 200                 205

Gly Pro Gly Pro Ser Ala Phe Ile Phe Pro Pro Lys Pro Lys Asp Thr
    210                 215                 220

Leu Met Ile Ser Arg Thr Pro Lys Val Thr Cys Val Val Val Asp Val
225                 230                 235                 240

Ser Gln Glu Asn Pro Glu Val Gln Phe Ser Trp Tyr Val Asp Gly Val
                245                 250                 255

Glu Val His Thr Ala Gln Thr Arg Pro Lys Glu Glu Gln Phe Asn Ser
            260                 265                 270

Thr Tyr Arg Val Val Ser Val Leu Pro Ile Gln His Gln Asp Trp Leu
        275                 280                 285

Asn Gly Lys Glu Phe Lys Cys Lys Val Asn Asn Lys Asp Leu Pro Ala
    290                 295                 300

Pro Ile Thr Arg Ile Ile Ser Lys Ala Lys Gly Gln Thr Arg Glu Pro
305                 310                 315                 320

Tyr Thr Leu Pro Pro Pro Thr Glu Glu Leu Ser Arg Ser Lys Val Thr
                325                 330                 335

Leu Thr Cys Leu Val Thr Gly Phe Tyr Pro Pro Asp Ile Asp Val Glu
            340                 345                 350

Trp Gln Arg Asn Gly Gln Pro Glu Pro Glu Gly Asn Tyr Arg Thr Thr
        355                 360                 365
```

```
Pro Pro Gln Gln Asp Val Asp Gly Thr Tyr Phe Leu Tyr Ser Lys Leu
    370                 375                 380

Ala Val Asp Lys Ala Ser Trp Gln Arg Gly Asp Thr Phe Gln Cys Ala
385                 390                 395                 400

Val Met His Glu Ala Leu His Asn His Tyr Thr Gln Lys Ser Ile Phe
                405                 410                 415

Lys Thr Pro Gly Lys
            420


<210> SEQ ID NO 43
<211> LENGTH: 413
<212> TYPE: PRT
<213> ORGANISM: Artificial Sequence
<220> FEATURE:
<223> OTHER INFORMATION: Amino acid sequence of interferon recombinant
      protein

<400> SEQUENCE: 43

Met Ala Pro Thr Ser Ala Phe Leu Thr Ala Leu Val Leu Leu Ser Cys
1               5                   10                  15

Asn Ala Ile Cys Cys Leu Gly Cys Asp Leu Pro Gln Thr His Ser Leu
            20                  25                  30

Ala His Thr Arg Ala Leu Arg Leu Leu Ala Gln Met Arg Arg Ile Ser
        35                  40                  45

Pro Phe Ser Cys Leu Asp His Arg Arg Asp Phe Gly Phe Pro Gln Glu
    50                  55                  60

Ala Leu Gly Gly Asn Gln Val Gln Lys Ala Gln Ala Met Ala Leu Val
65                  70                  75                  80

His Glu Met Leu Gln Gln Thr Phe Gln Leu Phe Ser Thr Glu Gly Ser
                85                  90                  95

Ala Ala Ala Trp Asp Glu Ser Leu Leu His Gln Phe Cys Thr Gly Leu
            100                 105                 110

Asp Gln Gln Leu Arg Asp Leu Glu Ala Cys Val Met Gln Glu Ala Glu
        115                 120                 125

Gly Thr Pro Leu Leu Glu Glu Asp Ser Ile Leu Ala Val Arg Lys Tyr
    130                 135                 140

Phe His Arg Leu Thr Leu Tyr Leu Gln Glu Lys Ser Tyr Ser Pro Cys
145                 150                 155                 160

Ala Trp Glu Ile Val Arg Ala Glu Val Met Arg Ala Phe Ser Ser Ser
                165                 170                 175

Arg Asn Leu Gly Ser Gly Ser Gly Ser Gly Thr Lys Thr Lys Pro Pro
            180                 185                 190

Cys Pro Ile Cys Pro Ala Cys Glu Gly Pro Gly Pro Ser Ala Phe Ile
        195                 200                 205

Phe Pro Pro Lys Pro Lys Asp Thr Leu Met Ile Ser Arg Thr Pro Lys
    210                 215                 220

Val Thr Cys Val Val Val Asp Val Ser Gln Glu Asn Pro Glu Val Gln
225                 230                 235                 240

Phe Ser Trp Tyr Val Asp Gly Val Glu Val His Thr Ala Gln Thr Arg
                245                 250                 255

Pro Lys Glu Glu Gln Phe Asn Ser Thr Tyr Arg Val Val Ser Val Leu
            260                 265                 270

Pro Ile Gln His Gln Asp Trp Leu Asn Gly Lys Glu Phe Lys Cys Lys
        275                 280                 285

Val Asn Asn Lys Asp Leu Pro Ala Pro Ile Thr Arg Ile Ile Ser Lys
    290                 295                 300
```

Ala Lys Gly Gln Thr Arg Glu Pro Tyr Thr Leu Pro Pro Pro Thr Glu
305 310 315 320

Glu Leu Ser Arg Ser Lys Val Thr Leu Thr Cys Leu Val Thr Gly Phe
325 330 335

Tyr Pro Pro Asp Ile Asp Val Glu Trp Gln Arg Asn Gly Gln Pro Glu
340 345 350

Pro Glu Gly Asn Tyr Arg Thr Thr Pro Pro Gln Gln Asp Val Asp Gly
355 360 365

Thr Tyr Phe Leu Tyr Ser Lys Leu Ala Val Asp Lys Ala Ser Trp Gln
370 375 380

Arg Gly Asp Thr Phe Gln Cys Ala Val Met His Glu Ala Leu His Asn
385 390 395 400

His Tyr Thr Gln Lys Ser Ile Phe Lys Thr Pro Gly Lys
405 410

<210> SEQ ID NO 44
<211> LENGTH: 422
<212> TYPE: PRT
<213> ORGANISM: Artificial Sequence
<220> FEATURE:
<223> OTHER INFORMATION: Amino acid sequence of interferon recombinant protein

<400> SEQUENCE: 44

Met Ala Pro Thr Ser Ala Phe Leu Thr Ala Leu Val Leu Leu Ser Cys
1 5 10 15

Asn Ala Ile Cys Cys Leu Gly Cys Asp Leu Pro Gln Thr His Ser Leu
20 25 30

Ala His Thr Arg Ala Leu Arg Leu Leu Ala Gln Met Arg Arg Ile Ser
35 40 45

Pro Phe Ser Cys Leu Asp His Arg Arg Asp Phe Gly Phe Pro Gln Glu
50 55 60

Ala Leu Gly Gly Asn Gln Val Gln Lys Ala Gln Ala Met Ala Leu Val
65 70 75 80

His Glu Met Leu Gln Gln Thr Phe Gln Leu Phe Ser Thr Glu Gly Ser
85 90 95

Ala Ala Ala Trp Asp Glu Ser Leu Leu His Gln Phe Cys Thr Gly Leu
100 105 110

Asp Gln Gln Leu Arg Asp Leu Glu Ala Cys Val Met Gln Glu Ala Glu
115 120 125

Gly Thr Pro Leu Leu Glu Glu Asp Ser Ile Leu Ala Val Arg Lys Tyr
130 135 140

Phe His Arg Leu Thr Leu Tyr Leu Gln Glu Lys Ser Tyr Ser Pro Cys
145 150 155 160

Ala Trp Glu Ile Val Arg Ala Glu Val Met Arg Ala Phe Ser Ser Ser
165 170 175

Arg Asn Leu Gly Gly Gly Gly Ser Gly Gly Gly Gly Ser Gly Gly Gly
180 185 190

Gly Ser Gly Thr Lys Thr Lys Pro Pro Cys Pro Ile Cys Pro Ala Cys
195 200 205

Glu Gly Pro Gly Pro Ser Ala Phe Ile Phe Pro Pro Lys Pro Lys Asp
210 215 220

Thr Leu Met Ile Ser Arg Thr Pro Lys Val Thr Cys Val Val Val Asp
225 230 235 240

Val Ser Gln Glu Asn Pro Glu Val Gln Phe Ser Trp Tyr Val Asp Gly

-continued

```
                245                 250                 255

Val Glu Val His Thr Ala Gln Thr Arg Pro Lys Glu Glu Gln Phe Asn
            260                 265                 270

Ser Thr Tyr Arg Val Val Ser Val Leu Pro Ile Gln His Gln Asp Trp
        275                 280                 285

Leu Asn Gly Lys Glu Phe Lys Cys Lys Val Asn Asn Lys Asp Leu Pro
    290                 295                 300

Ala Pro Ile Thr Arg Ile Ile Ser Lys Ala Lys Gly Gln Thr Arg Glu
305                 310                 315                 320

Pro Tyr Thr Leu Pro Pro Pro Thr Glu Glu Leu Ser Arg Ser Lys Val
                325                 330                 335

Thr Leu Thr Cys Leu Val Thr Gly Phe Tyr Pro Pro Asp Ile Asp Val
            340                 345                 350

Glu Trp Gln Arg Asn Gly Gln Pro Glu Pro Glu Gly Asn Tyr Arg Thr
        355                 360                 365

Thr Pro Pro Gln Gln Asp Val Asp Gly Thr Tyr Phe Leu Tyr Ser Lys
    370                 375                 380

Leu Ala Val Asp Lys Ala Ser Trp Gln Arg Gly Asp Thr Phe Gln Cys
385                 390                 395                 400

Ala Val Met His Glu Ala Leu His Asn His Tyr Thr Gln Lys Ser Ile
                405                 410                 415

Phe Lys Thr Pro Gly Lys
            420


<210> SEQ ID NO 45
<211> LENGTH: 411
<212> TYPE: PRT
<213> ORGANISM: Artificial Sequence
<220> FEATURE:
<223> OTHER INFORMATION: Amino acid sequence of interferon recombinant
      protein

<400> SEQUENCE: 45

Met Ala Pro Thr Ser Ala Phe Leu Thr Ala Leu Val Leu Leu Ser Cys
1               5                   10                  15

Asn Ala Ile Cys Cys Leu Gly Cys Asp Leu Pro Gln Thr His Ser Leu
            20                  25                  30

Ala His Thr Arg Ala Leu Arg Leu Leu Ala Gln Met Arg Arg Ile Ser
        35                  40                  45

Pro Phe Ser Cys Leu Asp His Arg Arg Asp Phe Gly Phe Pro Gln Glu
    50                  55                  60

Ala Leu Gly Gly Asn Gln Val Gln Lys Ala Gln Ala Met Ala Leu Val
65                  70                  75                  80

His Glu Met Leu Gln Gln Thr Phe Gln Leu Phe Ser Thr Glu Gly Ser
                85                  90                  95

Ala Ala Ala Trp Asp Glu Ser Leu Leu His Gln Phe Cys Thr Gly Leu
            100                 105                 110

Asp Gln Gln Leu Arg Asp Leu Glu Ala Cys Val Met Gln Glu Ala Glu
        115                 120                 125

Gly Thr Pro Leu Leu Glu Glu Asp Ser Ile Leu Ala Val Arg Lys Tyr
    130                 135                 140

Phe His Arg Leu Thr Leu Tyr Leu Gln Glu Lys Ser Tyr Ser Pro Cys
145                 150                 155                 160

Ala Trp Glu Ile Val Arg Ala Glu Val Met Arg Ala Phe Ser Ser Ser
                165                 170                 175
```

-continued

```
Arg Asn Leu Gly Gly Ser Gly Gly Thr Lys Thr Lys Pro Pro Cys Pro
            180                 185                 190

Ile Cys Pro Ala Cys Glu Gly Pro Gly Pro Ser Ala Phe Ile Phe Pro
        195                 200                 205

Pro Lys Pro Lys Asp Thr Leu Met Ile Ser Arg Thr Pro Lys Val Thr
    210                 215                 220

Cys Val Val Val Asp Val Ser Gln Glu Asn Pro Glu Val Gln Phe Ser
225                 230                 235                 240

Trp Tyr Val Asp Gly Val Glu Val His Thr Ala Gln Thr Arg Pro Lys
                245                 250                 255

Glu Glu Gln Phe Asn Ser Thr Tyr Arg Val Val Ser Val Leu Pro Ile
            260                 265                 270

Gln His Gln Asp Trp Leu Asn Gly Lys Glu Phe Lys Cys Lys Val Asn
        275                 280                 285

Asn Lys Asp Leu Pro Ala Pro Ile Thr Arg Ile Ile Ser Lys Ala Lys
    290                 295                 300

Gly Gln Thr Arg Glu Pro Tyr Thr Leu Pro Pro Pro Thr Glu Glu Leu
305                 310                 315                 320

Ser Arg Ser Lys Val Thr Leu Thr Cys Leu Val Thr Gly Phe Tyr Pro
                325                 330                 335

Pro Asp Ile Asp Val Glu Trp Gln Arg Asn Gly Gln Pro Glu Pro Glu
            340                 345                 350

Gly Asn Tyr Arg Thr Thr Pro Pro Gln Gln Asp Val Asp Gly Thr Tyr
        355                 360                 365

Phe Leu Tyr Ser Lys Leu Ala Val Asp Lys Ala Ser Trp Gln Arg Gly
    370                 375                 380

Asp Thr Phe Gln Cys Ala Val Met His Glu Ala Leu His Asn His Tyr
385                 390                 395                 400

Thr Gln Lys Ser Ile Phe Lys Thr Pro Gly Lys
                405                 410


<210> SEQ ID NO 46
<211> LENGTH: 415
<212> TYPE: PRT
<213> ORGANISM: Artificial Sequence
<220> FEATURE:
<223> OTHER INFORMATION: Amino acid sequence of interferon recombinant
      protein

<400> SEQUENCE: 46

Met Ala Pro Thr Ser Ala Phe Leu Thr Ala Leu Val Leu Leu Ser Cys
1               5                   10                  15

Asn Ala Ile Cys Cys Leu Gly Cys Asp Leu Pro Gln Thr His Ser Leu
            20                  25                  30

Ala His Thr Arg Ala Leu Arg Leu Leu Ala Gln Met Arg Arg Ile Ser
        35                  40                  45

Pro Phe Ser Cys Leu Asp His Arg Arg Asp Phe Gly Phe Pro Gln Glu
    50                  55                  60

Ala Leu Gly Gly Asn Gln Val Gln Lys Ala Gln Ala Met Ala Leu Val
65                  70                  75                  80

His Glu Met Leu Gln Gln Thr Phe Gln Leu Phe Ser Thr Glu Gly Ser
                85                  90                  95

Ala Ala Ala Trp Asp Glu Ser Leu Leu His Gln Phe Cys Thr Gly Leu
            100                 105                 110

Asp Gln Gln Leu Arg Asp Leu Glu Ala Cys Val Met Gln Glu Ala Glu
        115                 120                 125
```

Gly Thr Pro Leu Leu Glu Glu Asp Ser Ile Leu Ala Val Arg Lys Tyr
    130                 135                 140

Phe His Arg Leu Thr Leu Tyr Leu Gln Glu Lys Ser Tyr Ser Pro Cys
145                 150                 155                 160

Ala Trp Glu Ile Val Arg Ala Glu Val Met Arg Ala Phe Ser Ser Ser
                165                 170                 175

Arg Asn Leu Gly Gly Ser Gly Gly Gly Ser Gly Gly Thr Lys Thr Lys
            180                 185                 190

Pro Pro Cys Pro Ile Cys Pro Ala Cys Glu Gly Pro Gly Pro Ser Ala
        195                 200                 205

Phe Ile Phe Pro Pro Lys Pro Lys Asp Thr Leu Met Ile Ser Arg Thr
    210                 215                 220

Pro Lys Val Thr Cys Val Val Val Asp Val Ser Gln Glu Asn Pro Glu
225                 230                 235                 240

Val Gln Phe Ser Trp Tyr Val Asp Gly Val Glu Val His Thr Ala Gln
                245                 250                 255

Thr Arg Pro Lys Glu Glu Gln Phe Asn Ser Thr Tyr Arg Val Val Ser
            260                 265                 270

Val Leu Pro Ile Gln His Gln Asp Trp Leu Asn Gly Lys Glu Phe Lys
        275                 280                 285

Cys Lys Val Asn Asn Lys Asp Leu Pro Ala Pro Ile Thr Arg Ile Ile
    290                 295                 300

Ser Lys Ala Lys Gly Gln Thr Arg Glu Pro Tyr Thr Leu Pro Pro Pro
305                 310                 315                 320

Thr Glu Glu Leu Ser Arg Ser Lys Val Thr Leu Thr Cys Leu Val Thr
                325                 330                 335

Gly Phe Tyr Pro Pro Asp Ile Asp Val Glu Trp Gln Arg Asn Gly Gln
            340                 345                 350

Pro Glu Pro Glu Gly Asn Tyr Arg Thr Thr Pro Pro Gln Gln Asp Val
        355                 360                 365

Asp Gly Thr Tyr Phe Leu Tyr Ser Lys Leu Ala Val Asp Lys Ala Ser
    370                 375                 380

Trp Gln Arg Gly Asp Thr Phe Gln Cys Ala Val Met His Glu Ala Leu
385                 390                 395                 400

His Asn His Tyr Thr Gln Lys Ser Ile Phe Lys Thr Pro Gly Lys
                405                 410                 415

<210> SEQ ID NO 47
<211> LENGTH: 419
<212> TYPE: PRT
<213> ORGANISM: Artificial Sequence
<220> FEATURE:
<223> OTHER INFORMATION: Amino acid sequence of interferon recombinant protein

<400> SEQUENCE: 47

Met Ala Pro Thr Ser Ala Phe Leu Thr Ala Leu Val Leu Leu Ser Cys
1               5                   10                  15

Asn Ala Ile Cys Cys Leu Gly Cys Asp Leu Pro Gln Thr His Ser Leu
            20                  25                  30

Ala His Thr Arg Ala Leu Arg Leu Leu Ala Gln Met Arg Arg Ile Ser
        35                  40                  45

Pro Phe Ser Cys Leu Asp His Arg Arg Asp Phe Gly Phe Pro Gln Glu
    50                  55                  60

Ala Leu Gly Gly Asn Gln Val Gln Lys Ala Gln Ala Met Ala Leu Val

-continued

```
65                  70                  75                  80

His Glu Met Leu Gln Gln Thr Phe Gln Leu Phe Ser Thr Glu Gly Ser
                85                  90                  95

Ala Ala Ala Trp Asp Glu Ser Leu Leu His Gln Phe Cys Thr Gly Leu
            100                 105                 110

Asp Gln Gln Leu Arg Asp Leu Glu Ala Cys Val Met Gln Glu Ala Glu
        115                 120                 125

Gly Thr Pro Leu Leu Glu Glu Asp Ser Ile Leu Ala Val Arg Lys Tyr
    130                 135                 140

Phe His Arg Leu Thr Leu Tyr Leu Gln Glu Lys Ser Tyr Ser Pro Cys
145                 150                 155                 160

Ala Trp Glu Ile Val Arg Ala Glu Val Met Arg Ala Phe Ser Ser Ser
                165                 170                 175

Arg Asn Leu Gly Gly Ser Gly Gly Gly Ser Gly Gly Gly Ser Gly Gly
            180                 185                 190

Thr Lys Thr Lys Pro Pro Cys Pro Ile Cys Pro Ala Cys Glu Gly Pro
        195                 200                 205

Gly Pro Ser Ala Phe Ile Phe Pro Pro Lys Pro Lys Asp Thr Leu Met
    210                 215                 220

Ile Ser Arg Thr Pro Lys Val Thr Cys Val Val Val Asp Val Ser Gln
225                 230                 235                 240

Glu Asn Pro Glu Val Gln Phe Ser Trp Tyr Val Asp Gly Val Glu Val
                245                 250                 255

His Thr Ala Gln Thr Arg Pro Lys Glu Glu Gln Phe Asn Ser Thr Tyr
            260                 265                 270

Arg Val Val Ser Val Leu Pro Ile Gln His Gln Asp Trp Leu Asn Gly
        275                 280                 285

Lys Glu Phe Lys Cys Lys Val Asn Asn Lys Asp Leu Pro Ala Pro Ile
    290                 295                 300

Thr Arg Ile Ile Ser Lys Ala Lys Gly Gln Thr Arg Glu Pro Tyr Thr
305                 310                 315                 320

Leu Pro Pro Pro Thr Glu Glu Leu Ser Arg Ser Lys Val Thr Leu Thr
                325                 330                 335

Cys Leu Val Thr Gly Phe Tyr Pro Pro Asp Ile Asp Val Glu Trp Gln
            340                 345                 350

Arg Asn Gly Gln Pro Glu Pro Glu Gly Asn Tyr Arg Thr Thr Pro Pro
        355                 360                 365

Gln Gln Asp Val Asp Gly Thr Tyr Phe Leu Tyr Ser Lys Leu Ala Val
    370                 375                 380

Asp Lys Ala Ser Trp Gln Arg Gly Asp Thr Phe Gln Cys Ala Val Met
385                 390                 395                 400

His Glu Ala Leu His Asn His Tyr Thr Gln Lys Ser Ile Phe Lys Thr
                405                 410                 415

Pro Gly Lys
```

<210> SEQ ID NO 48
<211> LENGTH: 417
<212> TYPE: PRT
<213> ORGANISM: Artificial Sequence
<220> FEATURE:
<223> OTHER INFORMATION: Amino acid sequence of interferon recombinant protein

<400> SEQUENCE: 48

Met Ala Pro Thr Ser Ala Phe Leu Thr Ala Leu Val Leu Leu Ser Cys

-continued

```
1               5                   10                  15

Asn Ala Ile Cys Cys Leu Gly Cys Asp Leu Pro Gln Thr His Ser Leu
            20                  25                  30

Ala His Thr Arg Ala Leu Arg Leu Leu Ala Gln Met Arg Arg Ile Ser
        35                  40                  45

Pro Phe Ser Cys Leu Asp His Arg Arg Asp Phe Gly Phe Pro Gln Glu
    50                  55                  60

Ala Leu Gly Gly Asn Gln Val Gln Lys Ala Gln Ala Met Ala Leu Val
65                  70                  75                  80

His Glu Met Leu Gln Gln Thr Phe Gln Leu Phe Ser Thr Glu Gly Ser
                85                  90                  95

Ala Ala Ala Trp Asp Glu Ser Leu Leu His Gln Phe Cys Thr Gly Leu
            100                 105                 110

Asp Gln Gln Leu Arg Asp Leu Glu Ala Cys Val Met Gln Glu Ala Glu
        115                 120                 125

Gly Thr Pro Leu Leu Glu Glu Asp Ser Ile Leu Ala Val Arg Lys Tyr
    130                 135                 140

Phe His Arg Leu Thr Leu Tyr Leu Gln Glu Lys Ser Tyr Ser Pro Cys
145                 150                 155                 160

Ala Trp Glu Ile Val Arg Ala Glu Val Met Arg Ala Phe Ser Ser Ser
                165                 170                 175

Arg Asn Leu Gly Glu Asn Leu Tyr Phe Gln Ser Gly Gly Gly Thr Lys
            180                 185                 190

Thr Lys Pro Pro Cys Pro Ile Cys Pro Ala Cys Glu Gly Pro Gly Pro
        195                 200                 205

Ser Ala Phe Ile Phe Pro Pro Lys Pro Lys Asp Thr Leu Met Ile Ser
    210                 215                 220

Arg Thr Pro Lys Val Thr Cys Val Val Val Asp Val Ser Gln Glu Asn
225                 230                 235                 240

Pro Glu Val Gln Phe Ser Trp Tyr Val Asp Gly Val Glu Val His Thr
                245                 250                 255

Ala Gln Thr Arg Pro Lys Glu Glu Gln Phe Asn Ser Thr Tyr Arg Val
            260                 265                 270

Val Ser Val Leu Pro Ile Gln His Gln Asp Trp Leu Asn Gly Lys Glu
        275                 280                 285

Phe Lys Cys Lys Val Asn Asn Lys Asp Leu Pro Ala Pro Ile Thr Arg
    290                 295                 300

Ile Ile Ser Lys Ala Lys Gly Gln Thr Arg Glu Pro Tyr Thr Leu Pro
305                 310                 315                 320

Pro Pro Thr Glu Glu Leu Ser Arg Ser Lys Val Thr Leu Thr Cys Leu
                325                 330                 335

Val Thr Gly Phe Tyr Pro Pro Asp Ile Asp Val Glu Trp Gln Arg Asn
            340                 345                 350

Gly Gln Pro Glu Pro Glu Gly Asn Tyr Arg Thr Thr Pro Pro Gln Gln
        355                 360                 365

Asp Val Asp Gly Thr Tyr Phe Leu Tyr Ser Lys Leu Ala Val Asp Lys
    370                 375                 380

Ala Ser Trp Gln Arg Gly Asp Thr Phe Gln Cys Ala Val Met His Glu
385                 390                 395                 400

Ala Leu His Asn His Tyr Thr Gln Lys Ser Ile Phe Lys Thr Pro Gly
                405                 410                 415

Lys
```

<210> SEQ ID NO 49
<211> LENGTH: 443
<212> TYPE: PRT
<213> ORGANISM: Artificial Sequence
<220> FEATURE:
<223> OTHER INFORMATION: Amino acid sequence of interferon recombinant
      protein

<400> SEQUENCE: 49

```
Met Ala Pro Thr Ser Ala Phe Leu Thr Ala Leu Val Leu Leu Ser Cys
1               5                   10                  15

Asn Ala Ile Cys Cys Leu Gly Cys Asp Leu Pro Gln Thr His Ser Leu
            20                  25                  30

Ala His Thr Arg Ala Leu Arg Leu Leu Ala Gln Met Arg Arg Ile Ser
        35                  40                  45

Pro Phe Ser Cys Leu Asp His Arg Arg Asp Phe Gly Phe Pro Gln Glu
    50                  55                  60

Ala Leu Gly Gly Asn Gln Val Gln Lys Ala Gln Ala Met Ala Leu Val
65                  70                  75                  80

His Glu Met Leu Gln Gln Thr Phe Gln Leu Phe Ser Thr Glu Gly Ser
                85                  90                  95

Ala Ala Ala Trp Asp Glu Ser Leu Leu His Gln Phe Cys Thr Gly Leu
            100                 105                 110

Asp Gln Gln Leu Arg Asp Leu Glu Ala Cys Val Met Gln Glu Ala Glu
        115                 120                 125

Gly Thr Pro Leu Leu Glu Glu Asp Ser Ile Leu Ala Val Arg Lys Tyr
    130                 135                 140

Phe His Arg Leu Thr Leu Tyr Leu Gln Glu Lys Ser Tyr Ser Pro Cys
145                 150                 155                 160

Ala Trp Glu Ile Val Arg Ala Glu Val Met Arg Ala Phe Ser Ser Ser
                165                 170                 175

Arg Asn Leu Gly Gly Ser Ala Gly Gly Ser Gly Ser Gly Ser Ser Gly
            180                 185                 190

Gly Ser Ser Gly Ala Ser Gly Thr Gly Thr Ala Gly Gly Thr Gly Ser
        195                 200                 205

Gly Ser Gly Thr Gly Ser Gly Gly Thr Lys Thr Lys Pro Pro Cys Pro
    210                 215                 220

Ile Cys Pro Ala Cys Glu Gly Pro Gly Pro Ser Ala Phe Ile Phe Pro
225                 230                 235                 240

Pro Lys Pro Lys Asp Thr Leu Met Ile Ser Arg Thr Pro Lys Val Thr
                245                 250                 255

Cys Val Val Val Asp Val Ser Gln Glu Asn Pro Glu Val Gln Phe Ser
            260                 265                 270

Trp Tyr Val Asp Gly Val Glu Val His Thr Ala Gln Thr Arg Pro Lys
        275                 280                 285

Glu Glu Gln Phe Asn Ser Thr Tyr Arg Val Val Ser Val Leu Pro Ile
    290                 295                 300

Gln His Gln Asp Trp Leu Asn Gly Lys Glu Phe Lys Cys Lys Val Asn
305                 310                 315                 320

Asn Lys Asp Leu Pro Ala Pro Ile Thr Arg Ile Ile Ser Lys Ala Lys
                325                 330                 335

Gly Gln Thr Arg Glu Pro Tyr Thr Leu Pro Pro Pro Thr Glu Glu Leu
            340                 345                 350

Ser Arg Ser Lys Val Thr Leu Thr Cys Leu Val Thr Gly Phe Tyr Pro
        355                 360                 365
```

```
Pro Asp Ile Asp Val Glu Trp Gln Arg Asn Gly Gln Pro Glu Pro Glu
    370                 375                 380

Gly Asn Tyr Arg Thr Thr Pro Pro Gln Gln Asp Val Asp Gly Thr Tyr
385                 390                 395                 400

Phe Leu Tyr Ser Lys Leu Ala Val Asp Lys Ala Ser Trp Gln Arg Gly
                405                 410                 415

Asp Thr Phe Gln Cys Ala Val Met His Glu Ala Leu His Asn His Tyr
            420                 425                 430

Thr Gln Lys Ser Ile Phe Lys Thr Pro Gly Lys
        435                 440


<210> SEQ ID NO 50
<211> LENGTH: 443
<212> TYPE: PRT
<213> ORGANISM: Artificial Sequence
<220> FEATURE:
<223> OTHER INFORMATION: Amino acid sequence of interferon recombinant
      protein

<400> SEQUENCE: 50

Met Ala Pro Thr Ser Ala Phe Leu Thr Ala Leu Val Leu Leu Ser Cys
1               5                   10                  15

Asn Ala Ile Cys Cys Leu Gly Cys Asp Leu Pro Gln Thr His Ser Leu
            20                  25                  30

Ala His Thr Arg Ala Leu Arg Leu Leu Ala Gln Met Arg Arg Ile Ser
        35                  40                  45

Pro Phe Ser Cys Leu Asp His Arg Arg Asp Phe Gly Phe Pro Gln Glu
    50                  55                  60

Ala Leu Gly Gly Asn Gln Val Gln Lys Ala Gln Ala Met Ala Leu Val
65                  70                  75                  80

His Glu Met Leu Gln Gln Thr Phe Gln Leu Phe Ser Thr Glu Gly Ser
                85                  90                  95

Ala Ala Ala Trp Asp Glu Ser Leu Leu His Gln Phe Cys Thr Gly Leu
            100                 105                 110

Asp Gln Gln Leu Arg Asp Leu Glu Ala Cys Val Met Gln Glu Ala Glu
        115                 120                 125

Gly Thr Pro Leu Leu Glu Glu Asp Ser Ile Leu Ala Val Arg Lys Tyr
    130                 135                 140

Phe His Arg Leu Thr Leu Tyr Leu Gln Glu Lys Ser Tyr Ser Pro Cys
145                 150                 155                 160

Ala Trp Glu Ile Val Arg Ala Glu Val Met Arg Ala Phe Ser Ser Ser
                165                 170                 175

Arg Asn Leu Gly Gly Ser Gly Gly Gly Ser Glu Gly Gly Gly Ser Glu
            180                 185                 190

Gly Gly Gly Ser Glu Gly Gly Gly Ser Glu Gly Gly Gly Ser Glu Gly
        195                 200                 205

Gly Gly Ser Gly Gly Gly Ser Gly Thr Lys Thr Lys Pro Pro Cys Pro
    210                 215                 220

Ile Cys Pro Ala Cys Glu Gly Pro Gly Pro Ser Ala Phe Ile Phe Pro
225                 230                 235                 240

Pro Lys Pro Lys Asp Thr Leu Met Ile Ser Arg Thr Pro Lys Val Thr
                245                 250                 255

Cys Val Val Val Asp Val Ser Gln Glu Asn Pro Glu Val Gln Phe Ser
            260                 265                 270

Trp Tyr Val Asp Gly Val Glu Val His Thr Ala Gln Thr Arg Pro Lys
```

-continued

```
        275                 280                 285

Glu Glu Gln Phe Asn Ser Thr Tyr Arg Val Val Ser Val Leu Pro Ile
    290                 295                 300

Gln His Gln Asp Trp Leu Asn Gly Lys Glu Phe Lys Cys Lys Val Asn
305                 310                 315                 320

Asn Lys Asp Leu Pro Ala Pro Ile Thr Arg Ile Ile Ser Lys Ala Lys
                325                 330                 335

Gly Gln Thr Arg Glu Pro Tyr Thr Leu Pro Pro Pro Thr Glu Glu Leu
            340                 345                 350

Ser Arg Ser Lys Val Thr Leu Thr Cys Leu Val Thr Gly Phe Tyr Pro
        355                 360                 365

Pro Asp Ile Asp Val Glu Trp Gln Arg Asn Gly Gln Pro Glu Pro Glu
    370                 375                 380

Gly Asn Tyr Arg Thr Thr Pro Pro Gln Gln Asp Val Asp Gly Thr Tyr
385                 390                 395                 400

Phe Leu Tyr Ser Lys Leu Ala Val Asp Lys Ala Ser Trp Gln Arg Gly
                405                 410                 415

Asp Thr Phe Gln Cys Ala Val Met His Glu Ala Leu His Asn His Tyr
            420                 425                 430

Thr Gln Lys Ser Ile Phe Lys Thr Pro Gly Lys
        435                 440


<210> SEQ ID NO 51
<211> LENGTH: 433
<212> TYPE: PRT
<213> ORGANISM: Artificial Sequence
<220> FEATURE:
<223> OTHER INFORMATION: Amino acid sequence of interferon recombinant
      protein

<400> SEQUENCE: 51

Met Ala Pro Thr Ser Ala Phe Leu Thr Ala Leu Val Leu Leu Ser Cys
1               5                   10                  15

Asn Ala Ile Cys Cys Leu Gly Cys Asp Leu Pro Gln Thr His Ser Leu
            20                  25                  30

Ala His Thr Arg Ala Leu Arg Leu Leu Ala Gln Met Arg Arg Ile Ser
        35                  40                  45

Pro Phe Ser Cys Leu Asp His Arg Arg Asp Phe Gly Phe Pro Gln Glu
    50                  55                  60

Ala Leu Gly Gly Asn Gln Val Gln Lys Ala Gln Ala Met Ala Leu Val
65                  70                  75                  80

His Glu Met Leu Gln Gln Thr Phe Gln Leu Phe Ser Thr Glu Gly Ser
                85                  90                  95

Ala Ala Ala Trp Asp Glu Ser Leu Leu His Gln Phe Cys Thr Gly Leu
            100                 105                 110

Asp Gln Gln Leu Arg Asp Leu Glu Ala Cys Val Met Gln Glu Ala Glu
        115                 120                 125

Gly Thr Pro Leu Leu Glu Glu Asp Ser Ile Leu Ala Val Arg Lys Tyr
    130                 135                 140

Phe His Arg Leu Thr Leu Tyr Leu Gln Glu Lys Ser Tyr Ser Pro Cys
145                 150                 155                 160

Ala Trp Glu Ile Val Arg Ala Glu Val Met Arg Ala Phe Ser Ser Ser
                165                 170                 175

Arg Asn Leu Gly Gly Ser Gly Gly Ser Gly Gly Gly Gly Ser Gly Gly
            180                 185                 190
```

-continued

```
Gly Gly Ser Gly Gly Gly Gly Ser Gly Gly Gly Gly Ser Gly Thr Lys
        195                 200                 205

Thr Lys Pro Pro Cys Pro Ile Cys Pro Ala Cys Glu Gly Pro Gly Pro
    210                 215                 220

Ser Ala Phe Ile Phe Pro Pro Lys Pro Lys Asp Thr Leu Met Ile Ser
225                 230                 235                 240

Arg Thr Pro Lys Val Thr Cys Val Val Val Asp Val Ser Gln Glu Asn
                245                 250                 255

Pro Glu Val Gln Phe Ser Trp Tyr Val Asp Gly Val Glu Val His Thr
            260                 265                 270

Ala Gln Thr Arg Pro Lys Glu Glu Gln Phe Asn Ser Thr Tyr Arg Val
        275                 280                 285

Val Ser Val Leu Pro Ile Gln His Gln Asp Trp Leu Asn Gly Lys Glu
    290                 295                 300

Phe Lys Cys Lys Val Asn Asn Lys Asp Leu Pro Ala Pro Ile Thr Arg
305                 310                 315                 320

Ile Ile Ser Lys Ala Lys Gly Gln Thr Arg Glu Pro Tyr Thr Leu Pro
                325                 330                 335

Pro Pro Thr Glu Glu Leu Ser Arg Ser Lys Val Thr Leu Thr Cys Leu
            340                 345                 350

Val Thr Gly Phe Tyr Pro Pro Asp Ile Asp Val Glu Trp Gln Arg Asn
        355                 360                 365

Gly Gln Pro Glu Pro Glu Gly Asn Tyr Arg Thr Thr Pro Pro Gln Gln
    370                 375                 380

Asp Val Asp Gly Thr Tyr Phe Leu Tyr Ser Lys Leu Ala Val Asp Lys
385                 390                 395                 400

Ala Ser Trp Gln Arg Gly Asp Thr Phe Gln Cys Ala Val Met His Glu
                405                 410                 415

Ala Leu His Asn His Tyr Thr Gln Lys Ser Ile Phe Lys Thr Pro Gly
            420                 425                 430

Lys
```

RECOMBINANT FUSION INTERFERON FOR ANIMALS

CROSS-REFERENCE TO RELATED APPLICATIONS

This application is a continuation-in-part of U.S. patent application Ser. No. 13/557,139, filed Jul. 24, 2012, entitled "RECOMBINANT FUSION INTERFERON FOR ANIMALS" by Tsun-Yung Kuo, Chung-Chin Wu, and Han-Ting Chen. The disclosure of the above identified co-pending application is incorporated herein by reference in its entirety.

Some references, if any, which may include patents, patent applications and various publications, may be cited and discussed in the description of this invention. The citation and/or discussion of such references, if any, is provided merely to clarify the description of the present invention and is not an admission that any such reference is "prior art" to the invention described herein. All references listed, cited and/or discussed in this specification are incorporated herein by reference in their entireties and to the same extent as if each reference was individually incorporated by reference.

FIELD OF THE INVENTION

The present invention relates to a recombinant fusion interferon for animals, particularly to a recombinant fusion interferon having antiviral activities against animal viruses.

BACKGROUND OF THE INVENTION

Interferon (IFN) is initially discovered in 1957 by Alick Isaacs and Jean Lindenmann during research of influenza virus. After infected by virus, the host cells immediately secrete a cytokine to induce other cells nearby to produce antiviral proteins to interfere with viral replication. This cytokine is later named IFN. Since the first discovery of IFN, three types of IFN have been identified—type I IFN (IFN-α and IFN-β), type II IFN (IFN-γ), and type III IFN (IFN-λ). The antiviral effects of IFN are mainly provided by type I IFN (IFN-α and IFN-β). In addition to antiviral activities, IFN has anti-tumor activity, and can induce cell differentiation and modulate immune response.

So far, the majority of commercial IFN is used for the treatment of human diseases, such as human hepatitis B, human hepatitis C, Kaposi's sarcoma (KS), and malignant melanoma.

Without an effective vaccine for preventing an animal virus, an infected animal of the virus can only be treated with supportive therapy. However, supportive therapy is usually ineffective, and therefore the infection of animal virus may cause great economic losses in livestock husbandry.

Therefore, it is important to develop IFN having antiviral activities against animal viruses.

SUMMARY OF THE INVENTION

The first aspect of the present invention relates to a recombinant fusion IFN for animals. IFN possesses a short serum half-life (about 2 to 8 hours) due to its small molecular size. The present invention provides a stably recombinant fusion IFN for animals in which a porcine IFN is fused with a porcine immunoglobulin Fc fragment (IgG Fc) possessing a long serum half-life. The porcine IgG Fc is fused with the N-terminus or the C-terminus of the porcine IFN. The porcine IFN and the porcine IgG Fc can be further joined by a peptide linker. Therefore, the recombinant fusion IFN of the present invention is represented by formula (I) or formula (II)

(Porcine interferon)-(Linker)$_n$-(Porcine immunoglobulin Fc fragment) (I)

(Porcine immunoglobulin Fc fragment)-(Linker)$_n$-(Porcine Interferon) (II)

where:

the porcine interferon has at least 85%, preferably 90%, even more preferably 91%, 92%, 93%, 94%, 95%, 96%, 97%, 98%, 99% sequence identity with the sequences of SEQ ID NOs: 1, 2, 3, 4, 5, 6, 7, 8, 9, 10, 11, 12, 13, 14, 15, 16, and 17;

the porcine immunoglobulin Fc fragment has at least 85%, preferably 90%, even more preferably 91%, 92%, 93%, 94%, 95%, 96%, 97%, 98%, 99% sequence identity with the sequences of SEQ ID NOs: 18, 19, 20, 21, and 22;

the linker has at least one glycine, and the linker has a sequence including, but not limited to, glycine-glycine, glycine-serine, the sequences of SEQ ID NOs: 23, 24, 25, 26, 27, 28, 29, 30, 31, and 32;

n is 0, 1, 2, 3, 4, 5, 6, 7, 8, 9, or 10; and the recombinant fusion IFN specifically binds an antibody that specifically binds porcine interferon and an antibody that specifically binds porcine immunoglobulin Fc fragment.

In one embodiment, the porcine IFN encodes an amino acid sequence of SEQ ID NOs: 1, 2, 3, 4, 5, 6, 7, 8, 9, 10, 11, 12, 13, 14, 15, 16, or 17. The porcine IgG Fc encodes an amino acid sequence of SEQ ID NOs: 18, 19, 20, 21, or 22. The linker encodes an amino acid sequence of SEQ ID NOs: 23, 24, 25, 26, 27, 28, 29, 30, 31, or 32. In one example, the recombinant fusion IFN has a sequence from any one of SEQ ID NOs: 41-51. Each of the SEQ ID NOs: 41-51 includes a SEQ IN NO: 2, any one of the SEQ ID NOs: 23-32, and a SEQ ID NO: 22.

In one preferred embodiment, the porcine IFN encodes an amino acid sequence of SEQ ID NO: 1, the porcine IgG Fc encodes an amino acid sequence of SEQ ID NO: 22, and the linker encodes an amino acid sequence of SEQ ID NO: 23.

In another preferred embodiment, the porcine IFN encodes an amino acid sequence of SEQ ID NO: 2, the porcine IgG Fc encodes an amino acid sequence of SEQ ID NO: 18, and the linker encodes an amino acid sequence of SEQ ID NO: 23.

The recombinant fusion IFN of the present invention is made by gene cloning technology. A DNA sequence encoding a porcine IFN and a DNA sequence encoding a porcine IgG Fc are cloned into an expression vector to obtain a polynucleotide encoding the recombinant fusion IFN. The vector containing the polynucleotide encoding the recombinant fusion IFN is then introduced to a host cell where the recombinant fusion IFN can be expressed. An additional DNA sequence encoding a peptide linker having glycine and serine residues can be further cloned into the expression vector to join the DNA sequence encoding a porcine IFN and the DNA sequence encoding a porcine IgG Fc.

The expression vector can be a prokaryotic expression vector or a eukaryotic expression vector. The prokaryotic expression vector includes, but is not limited to, pET, pGEX, and pDEST expression vectors. The eukaryotic expression vector includes, but is not limited to, pSecTag, pcDNA3, pCMV-Script, pCI, and pSV40b expression vectors.

The host cell can be a prokaryotic cell, such as bacteria, or a eukaryotic cell, such as yeast, insect cells, plant cells, and mammalian cells. An example of bacteria includes, but not limited to, *Escherichia coli* (*E. coli.*). An example of mammalian cells that can be used to express the recombinant fusion IFN of the present invention includes, but are not limited to, 3T3 cells, Chinese hamster ovary cells (CHO cells), baby hamster kidney cells (BHK cells), human cervical cancer cells (such as Hela cells), and human liver carcinoma cells (such as HepG2 cells).

The second aspect of the present invention relates to a composition comprising the recombinant fusion IFN of the present invention and a pharmaceutically acceptable excipient.

The excipient may be pharmaceutically acceptable organic or inorganic carrier substances suitable for parenteral, enteral or intranasal application which do not deleteriously react with the active compounds and are not deleterious to the recipient thereof. Suitable excipients include, but are not limited to, water, salt solutions, vegetable oils, polyethylene glycols, gelatin, lactose, amylose, magnesium stearate, talc, silicic acid, viscous paraffin, fatty acid monoglycerides and diglycerides, petroethral fatty acid esters, hydroxymethyl-cellulose, polyvinylpyrrolidone, etc. In one embodiment, the excipient is phosphate buffer solution (PBS).

The third aspect of the present invention relates to a method for treating or inhibiting virus infection in an animal. In one embodiment, the method comprises administering a composition comprising the recombinant fusion IFN of the present invention to an animal. The virus may be an animal DNA virus or an animal RNA virus. The animal virus includes, but is not limited to, pseudorabies virus (PRV), porcine reproductive and respiratory syndrome virus (PRRSV), parvovirus, Transmissible gastroenteritis coronavirus (TGEV), Japanese encephalitis virus (JEV), Rotavirus, Porcine circovirus type 2 (PCV2), foot and mouth disease virus (FMDV), hog cholera virus (HCV), African swine fever virus, swinepox virus, porcine cytomegalovirus, porcine epidemic diarrhea virus, swine vesicular disease virus, porcine teschovirus, procine astrovirus. The animal may be an animal infected with an animal virus or an animal not infected with an animal virus. In another embodiment, the composition further comprises a pharmaceutically acceptable excipient.

These and other aspects of the present invention will become apparent from the following description of the preferred embodiment taken in conjunction with the following drawings, although variations and modifications therein may be effected without departing from the spirit and scope of the novel concepts of the disclosure.

DETAILED DESCRIPTION OF THE PREFERRED EMBODIMENT

The present invention is more particularly described in the following examples that are intended as illustrative only since numerous modifications and variations therein will be apparent to those skilled in the art. Various embodiments of the invention are now described in detail. Referring to the drawings, like numbers indicate like components throughout the views.

As used in the description herein and throughout the claims that follow, the meaning of "a", "an", and "the" includes plural reference unless the context clearly dictates otherwise. Moreover, titles or subtitles may be used in the specification for the convenience of a reader, which shall have no influence on the scope of the present invention.

The terms "treat," "treating," "treatment," and the like are used herein to refer to prevention or partially preventing a disease, symptom, or condition and/or a partial or complete cure or relief of a disease, condition, symptom, or adverse effect attributed to the disease. Thus, the terms "treat," "treating," "treatment," and the like refer to both prophylactic and therapeutic treatment regimes.

The terms "inhibit," "inhibiting," "inhibition," and the like are used herein to refer to a reduction or decrease in a quality or quantity, compared to a baseline. For example, in the context of the present invention, inhibition of viral replication refers to a decrease in viral replication as compared to baseline. Similarly, inhibiting virus infection refers to a decrease in virus infection as compared to baseline.

The term "antiviral activity" is used herein to refer to that the IFN can inhibit or interfere the biological activity of virus.

The term "biological activity of virus" is used herein to refer to virus infection, replication, and the like.

The meaning of the technical and scientific terms as described herein can be clearly understood by a person of ordinary skill in the art.

EXAMPLE 1

Molecular Cloning of Porcine Interferon

Peripheral blood mononuclear cells (PBMCs) were firstly isolated from blood of a pig (L×Y-D strain). A total RNA was isolated from the PBMCs by the guanidine thiocyanate (GTC) method and then was used in a reverse transcription polymerase chain reaction (RT-PCR) to generate complementary DNA (cDNA). The cDNA was then used as DNA template to amplify porcine interferon genes by polymerase chain reaction (PCR). A forward primer and a reverse primer were designed to amplify the porcine interferon nucleotide sequence. The forward primer in this example has a HindIII cleavage site, and the reverse primer in this example has an Xho I cleavage site. The primers for cloning porcine interferon genes are the following:

```
Forward primer (IFN-F1):
                                   (SEQ ID NO: 34)
5'-CCCAAGCTTATGGCCCCAACCTCAGCC-3'
       HindIII

Reverse primer (IFN-R1):
                                   (SEQ ID NO: 35)
5'-CCCCTCGAGCAGGTTTCTGGAGGAAGA-3'
       XhoI
```

The PCR was carried out as follows: inactivation of cDNA at 95° C. for 5 minutes, amplification of porcine interferon genes by Taq polymerase with 30 cycles of 95° C. for 1 minute, 55° C. for 30 seconds, 72° C. for 30 seconds, and final extension at 72° C. for 5 minutes.

The PCR products were then constructed into a pET20b expression vector with the restriction enzyme cutting sites, Hind III and Xho I. Plasmids containing the PCR products were transformed into host cells (*E. coli*). Transformants were selected and sequenced, and then the DNA sequences of the PCR products were translated into amino acid sequences. Seventeen (17) different amino acid sequences of porcine interferon were cloned, and their sequence are shown as SEQ ID NOs: 1, 2, 3, 4, 5, 6, 7, 8, 9, 10, 11, 12, 13, 14, 15, 16, and 17.

EXAMPLE 2

Synthesis of Porcine Recombinant Fusion Interferon

The porcine interferon genes cloned in Example 1 were used to synthesize the porcine recombinant fusion interferon of the present invention. DNA sequences encoding the recombinant fusion interferon were synthesized by a DNA synthesizer. The recombinant fusion interferon is represented by formula (I) or formula (II)

(Porcine interferon)-$(Linker)_n$-(Porcine immunoglobulin Fc fragment) (I)

(Porcine immunoglobulin Fc fragment)-$(Linker)_n$-(Porcine Interferon) (II)

where:

the porcine interferon encodes an amino acid sequence of SEQ ID NOs: 1, 2, 3, 4, 5, 6, 7, 8, 9, 10, 11, 12, 13, 14, 15, 16, or 17;

the porcine immunoglobulin Fc fragment encodes an amino acid sequence of SEQ ID NOs: 18, 19, 20, 21, and 22;

the linker has a sequence of glycine-glycine, glycine-serine, or the sequences of SEQ ID NOs: 23, 24, 25, 26, 27, 28, 29, 30, 31, 32, or 33; and n is 0, 1, 2, 3, 4, 5, 6, 7, 8, 9, or 10.

An EcoRV site at the 5' end and a HindIII site at the 3' end were added to the DNA sequences of the porcine recombinant fusion interferon when the DNA sequences were synthesized. The synthesized DNA sequences were then constructed into a pcDNA3 expression vector with the restriction enzyme cutting sites, EcoRV and Hind III. Plasmids containing the synthesized DNA sequences were transformed into host cells (*E. coli*).

The pcDNA3 expression vectors containing the synthesized DNA sequences were then transfected into CHO cells using Lipofectamine (Invitrogen) according to the manufacturer's instructions. The transfected CHO cells were then cultivated at 37° C., 5% $CO_2$ in F12 medium containing 10% fetal bovine serum (FBS) for 48 hours.

After that, the transfected CHO cells were cultivated at 37° C., 5% $CO_2$ in F12 medium with 10% FBS, 100 units/ml penicillin, 100 units/ml streptomycin, and 100-700 μg/ml Zeocin to select cells comprising the porcine recombinant fusion IFN gene. The selective medium was replenished every 3 to 4 days until 10 to 20% of cells survived. The surviving cells were cultivated in F12 medium with 10% FBS until the cells grew to near confluence. Expression of the porcine recombinant fusion IFN from the selective cells was then detected by Western blot with proper antibodies.

Sample cells were cultivated in F-12 medium with 10% FBS for 72 hours, and then the supernatant was collected and analyzed by sodium dodecyl sulfate-polyacrylamide gel electrophoresis (SDS-PAGE). For protein immunoblotting, following electrophoresis, proteins were transferred to a PVDF membrane. The resulting membrane was blocked with 5% skim milk in TBST (10 mM Tris-HCl pH 8.0, 150 mM NaCl, 0.3% Tween 20) at 4° C. for 16 to 24 hours to prevent non-specific binding of proteins and then washed 3 times with TBST. The membrane was then incubated with mouse anti IFNα monoclonal antibody (SANTA CRUZ) (1:500 dilution in TBST containing 0.5% skin milk) at room temperature for 1 hour. The blots were then washed 6 times with TBST and incubated with alkaline phosphatase (AP) conjugated goat anti-mouse IgG monoclonal antibody (1:2000 dilution in TBST containing 0.5% skin milk) at room temperature for 1 hour. The blots were then washed 6 times with TBST. The bands were detected using nitro blue tetrazolium (NBT)/5-bromo-4-chloro-3-indolyl-phosphate (BCIP) substrate for 5 minutes and then washed with water to stop the reaction. In addition, the porcine recombinant fusion IFN (P IFN-Fc) was also detected using alkaline phosphatase (AP) conjugated goat anti-porcine IgG antibody (KPL) and using alkaline phosphatase (AP) conjugated mouse anti 6× His monoclonal antibody (invitrogen).

Protein expressed in CHO cells that were transfected with a DNA sequence of the porcine recombinant fusion IFN is confirmed by Western blots. The porcine recombinant fusion IFN detected has the following formula: (Porcine interferon)-$(Linker)_1$-(Porcine immunoglobulin Fc fragment), where the porcine interferon encodes an amino acid sequence of SEQ ID NO: 1, the porcine immunoglobulin Fc fragment encodes an amino acid sequence of SEQ ID NO: 22, and the linker encodes an amino acid sequence of SEQ ID NO: 23. The porcine recombinant fusion IFN was detected by mouse anti IFNα monoclonal antibody, mouse anti 6× His monoclonal antibody, and goat anti-porcine IgG antibody. The results show that transfected CHO cells secrete the porcine recombinant fusion IFN (SEQ ID NO: 1-SEQ ID NO: 23-SEQ ID NO: 22).

Protein expressed in CHO cells that were transfected with another DNA sequence of the porcine recombinant fusion IFN is confirmed by Western blots. The porcine recombinant fusion IFN detected has the following formula: (Porcine interferon)-$(Linker)_1$-(Porcine immunoglobulin Fc fragment), where the porcine interferon encodes an amino acid sequence of SEQ ID NO: 2, the porcine immunoglobulin Fc fragment encodes an amino acid sequence of SEQ ID NO: 22, and the linker encodes an amino acid sequence of SEQ ID NO: 33. The porcine recombinant fusion IFN was detected by mouse anti IFNα monoclonal antibody and goat anti-porcine IgG antibody. The results show that transfected CHO cells secrete the porcine recombinant fusion IFN of SEQ ID NO: 51 (SEQ ID NO: 2-SEQ ID NO: 33-SEQ ID NO: 22).

EXAMPLE 3

Production of Porcine Recombinant Fusion IFN

CHO cells transfected with the porcine recombinant fusion IFN (SEQ ID No: 1-SEQ ID No: 23-SEQ ID No: 22) was seeded at a density of $2\times10^6$ cells in a 25 $cm^2$ cell culture flask and cultivated in F12 medium with 10% FBS, 100 units/ml penicillin, and 100 units/ml streptomycin for 24 hours. The medium was then removed. The cells were washed with PBS and then cultivated in F12 medium with 1% FBS, 100 units/ml penicillin, and 100 units/ml streptomycin. Supernatant was collected and fresh medium containing 1% FBS, penicillin, and streptomycin was added every 72 hours. The supernatant containing the porcine recombinant fusion IFN was centrifuged (1,000 rpm) for 10 minutes to remove cells and cell debris.

EXAMPLE 4

Analysis of Antiviral Activities Against PRRSV of the Porcine Recombinant Fusion IFN The porcine recombinant fusion IFN obtained in Example 3 was diluted serially (10, 20, 40, 80, 160, 320, 640, 1280, and 2560-folds) with minimum essential media (MEM medium) containing 1% FBS, 100 units/ml penicillin, and 100 units/ml streptomycin. MARC-145 cells were seeded at a density of $1.5\times10^4$ cells/well in 96-well cell culture plates and cultivated at 37° C., 5% $CO_2$ for 16 to 24 hours. After the culture medium was removed, the cells were treated with the diluted porcine recombinant fusion IFN or porcine interferon having an amino acid sequence of SEQ ID NO: 1 (100 μl/well, n=4), and then cultivated at 37° C., 5% $CO_2$ for 24 hours. After the diluted samples were removed, the cells were infected with PRRS virus (100 $TCID_{50}$/100 μl) and then cultivated at 37°

C., 5% $CO_2$ for 4-5 days. Then cells were used to evaluate the antiviral activity of the porcine recombinant fusion IFN by MTT assay.

Cell suspension was removed, and the cells were washed twice with PBS and then fixed on the plate with 80% acetone (−20° C., 100 μl/well) at 4° C. for 30 minutes. After acetone was removed, the cells were washed 3 times with PBS and stained with 1% methylrosaniline chloride for 20 minutes. After that, the cells were washed 5 times with distilled water, and then 100% ethanol was added to dissolve methylrosaniline chloride. 10 minutes later, the absorbance of the signals was read using an ELISA reader set at 550 nm. Concentration of the porcine recombinant fusion IFN (P IFN-Fc) was calculated by the following formulas.

$$\frac{OD\text{ maximum}+OD\text{ minimum}}{2}=OD50\% \qquad \text{Formula 1}$$

where OD maximum is absorbancy of uninfected cell monolayers treated or untreated with IFN (protection 100%), and OD minimum is absorbancy of the infected non-protected cell monolayer (protection zero).

$$IFN\text{ titer}(\text{U ml}^{-1})=T_n+\left[(T_{n+1}-T_n)\times\frac{(OD_n-OD50\%)}{(OD_n-OD_{n+1})}\right] \qquad \text{Formula 2}$$

where $T_n$ is reciprocal of the IFN dilution corresponding to OD immediately higher than OD50%, $T_{n+1}$ is reciprocal of the IFN dilution corresponding to OD immediately lower than the OD50%, $OD_n$ is the absorbancy values immediately higher than OD50%, and $OD_{n+1}$ is the absorbancy values immediately lower than OD50%.

Table 1 show the results of the assays of antiviral activity against PRRSV of the porcine recombinant fusion IFN and the porcine IFN. The results show that the porcine recombinant fusion IFN possesses a higher antiviral activity against PRRSV than the porcine IFN.

TABLE 1

Comparison of antiviral activities against PRRSV of the porcine recombinant fusion IFN and the porcine IFN.

| Treatment | Antiviral Activities Against PRRSV (IU/ml) |
|---|---|
| Porcine recombinant fusion IFN | 3147 |
| Porcine IFN | 1500 |

EXAMPLE 5

Analysis of Antiviral Activities Against PRV of the Porcine Recombinant Fusion IFN The porcine recombinant fusion IFN obtained in Example 3 was diluted serially (10, 20, 40, 80, 160, 320, 640, 1280, and 2560-folds) with minimum essential media (MEM medium) containing 1% FBS, 100 units/ml penicillin, and 100 units/ml streptomycin. ST cells were cultivated at a density of $1.5\times10^4$ cells/well in 96-well cell culture plates at 37° C., 5% $CO_2$ for 16 to 24 hours. After the culture medium was removed, the cells were treated with the porcine recombinant fusion IFN obtained in Example 3 or the porcine IFN encoding an amino acid sequence of SEQ ID NO. 1 for 16 to 24 hours. After the two types of IFN were removed, the cells were infected with PR virus (1 $TCID_{50}$/100 μl) and then cultivated at 37° C., 5% $CO_2$ for 4 to 5 days. Then cell viabilities were analyzed by MTT method, which is described in Example 4.

Table 2 and show the results of the assays of antiviral activity against PRV of the porcine recombinant fusion IFN and the porcine IFN. The results show that the porcine recombinant fusion IFN possesses a higher antiviral activity against PRV than the porcine IFN.

TABLE 2

Comparison of antiviral activities against PRV of the porcine recombinant fusion IFN and the porcine IFN.

| Treatment | Antiviral Activities Against PRRSV (IU/ml) |
|---|---|
| Porcine recombinant fusion IFN | 4000 |
| Porcine IFN | 960 |

EXAMPLE 6

Analysis of Antiviral Activities Against Porcine Parvovirus of the Porcine Recombinant Fusion IFN The porcine recombinant fusion IFN obtained in Example 3 was diluted serially (10, 20, 40, 80, 160, 320, 640, 1280, and 2560-folds) with minimum essential media (MEM medium) containing 1% FBS, 100 units/ml penicillin, and 100 units/ml streptomycin. ST cells were cultivated at a density of $1\times10^4$ cells/well in 96-well cell culture plates at 37° C., 5% $CO_2$ for 24 hours. After the culture medium was removed, the cells were treated with the diluted porcine recombinant fusion IFN for 24 hours. After the two types of IFN were removed, the cells were infected with porcine parvovirus (100 $TCID_{50}$/100 μl) and then cultivated at 37° C., 5% $CO_2$ for 5 days. Then cell viabilities were analyzed by MTT method, which is described in Example 4.

The antiviral activities against porcine parvovirus of the porcine recombinant fusion IFN obtained in Example 3 is 3101 IU/ml. The result shows that the porcine recombinant fusion IFN possesses an antiviral activity against PRV.

Based on the results of the Examples above, the recombinant fusion IFN of the present invention possesses higher antiviral activities against both RNA virus and DNA virus than a porcine IFN.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments are chosen and described in order to explain the principles of the invention and their practical application so as to activate others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

What is claimed is:

1. A porcine recombinant fusion interferon represented by [formula (I), (Porcine interferon)-(Linker)n-(Porcine immunoglobulin Fc fragment)] porcine interferon-linker-porcine immunoglobulin Fc fragment [(I), and] comprising an amino acid sequence selected from SEQ ID NOs: 41-47, wherein [n is 0, 1, 2, 3, 4, 5, 6, 7, 8, 9, or 10; and] the porcine recombinant fusion interferon specifically binds an antibody that specifically binds the porcine interferon and an antibody that specifically binds the porcine immunoglobulin Fc fragment.

2. A pharmaceutical composition for treating or inhibiting virus infection in an animal, comprising the porcine recombinant fusion interferon of claim 1 and a pharmaceutically acceptable excipient.

* * * * *